US012721811B1

(12) United States Patent
Gande et al.

(10) Patent No.: US 12,721,811 B1
(45) Date of Patent: Sep. 1, 2026

(54) STABLE LYOPHILIZED COMPOSITION OF PEMETREXED DIPOTASSIUM

(71) Applicant: AVYXA Pharma, Parsippany, NJ (US)

(72) Inventors: Mukteeshwar Gande, Monroe, NJ (US); Praveen Reddy Billa, Flanders, NJ (US)

(73) Assignee: AVYXA Pharma

( * ) Notice: Subject to any disclaimer, the term of this patent is extended or adjusted under 35 U.S.C. 154(b) by 0 days.

(21) Appl. No.: 19/249,629

(22) Filed: Jun. 25, 2025

(51) Int. Cl.

| | |
|---|---|
| ***A61K 9/08*** | (2006.01) |
| ***A61K 9/00*** | (2006.01) |
| ***A61K 9/14*** | (2006.01) |
| ***A61K 9/19*** | (2006.01) |
| ***A61K 31/519*** | (2006.01) |
| ***A61K 47/26*** | (2006.01) |

(52) U.S. Cl.
CPC .............. *A61K 9/08* (2013.01); *A61K 9/0019* (2013.01); *A61K 9/143* (2013.01); *A61K 9/145* (2013.01); *A61K 9/19* (2013.01); *A61K 31/519* (2013.01); *A61K 47/26* (2013.01)

(58) Field of Classification Search
CPC ........ A61K 9/08; A61K 9/0019; A61K 9/143; A61K 9/145; A61K 9/19; A61K 31/519; A61K 47/26
See application file for complete search history.

(56) References Cited

U.S. PATENT DOCUMENTS

| | | | | |
|---|---|---|---|---|
| 5,344,932 | A | 9/1994 | Taylor | |
| 9,421,207 | B2 | 8/2016 | Khattar et al. | |
| 9,789,113 | B2 | 10/2017 | Shivakumar et al. | |
| 2011/0201631 | A1* | 8/2011 | Kocherlakota ......... | A61P 35/00 544/280 |
| 2015/0359898 | A1* | 12/2015 | Purandare ............ | A61K 31/519 536/123.13 |
| 2017/0100403 | A1* | 4/2017 | Shivakumar ......... | A61K 31/519 |

FOREIGN PATENT DOCUMENTS

| | | | |
|---|---|---|---|
| CN | 103784454 | A | 11/2015 |
| CN | 105726492 | A | 7/2016 |
| JP | 6854710 | B2 | 10/2019 |
| WO | 200156575 | A1 | 8/2001 |
| WO | 2018002956 | A1 | 1/2018 |

OTHER PUBLICATIONS

Warner et al., Development of a purity control strategy for pemetrexed disodium and validation of associated analytical methodology, Journal of Pharmaceutical and Biomedical Analysis, 2015, 46-56, (105).
Zhang et al., Physical and Chemical Stability of Pemetrexed in Infusion Solutions, the Annals of Pharmacotherapy , 2006, 1082-1085, (40).
Saravanan et al., Stability-Indicating LC Assay Method for Pemetrexed Disodium, Chromatographia 2007, 431-434, (66).
Liu et al., Development and validation of a combined potency assay and enantiomeric purity method for a chiral pharmaceutical compound using capillary electrophoresis, Journal of Chromatography A, 1996, 45-52, ( 745).
Won et al., Effect of Formulation Factors and Oxygen Levels on the Stability of Aqueous Injectable Solution Containing Pemetrexed, Pharmaceutics, 2020; 12(1):46. doi: 10.3390/pharmaceutics12010046).
Nekkalapudi et. al., Eco-Friendly Stability-Indicating HPLC Method for Related Compounds in Pemetrexed Ditromethamine (Antineoplastic Agent) for Injection, Journal of AOAC International, 2024, 107(3), 415-429.
Prescribing Information for PEMETREXED for injection; 38 pages.

* cited by examiner

*Primary Examiner* — Bethany P Barham
*Assistant Examiner* — Janet Joseph
(74) *Attorney, Agent, or Firm* — The Belles Group, P.C.

(57) ABSTRACT

The present invention relates to a stable, lyophilized pharmaceutical composition comprising pemetrexed dipotassium, mannitol, and a pH modifying component consisting essentially of hydrochloric acid. The composition is designed for ease of reconstitution and demonstrates long-term stability. Specifically, when stored in sealed and sterile vials at 25° C., the composition maintains its integrity for 12 months and more. Also, described here in the method of treating non-squamous NSCLC or mesothelioma using the composition of invention.

16 Claims, No Drawings

STABLE LYOPHILIZED COMPOSITION OF PEMETREXED DIPOTASSIUM

FIELD OF THE DISCLOSURE

The present invention discloses a reconstitutable lyophilized composition comprising pemetrexed dipotassium, mannitol and a pH modifying component consisting essentially of hydrochloric acid; wherein after storage for at least 12 months at a temperature of 25° C. in a sealed and sterile vial, the composition contains minimal total impurities.

BACKGROUND

Pemetrexed is used in the treatment of malignant pleural mesothelioma and non-small cell lung cancer. U.S. Pat. No. 5,344,932B2 discloses the antifolate compound known as "Pemetrexed" which is used as an anti-cancer agent. This member of the folic acid family has been approved for the treatment of malignant pleural mesothelioma and for second-line treatment of non-small cell lung cancer. Pemetrexed disodium heptahydrate salt represented by Formula I is marketed by Eli Lilly and Company under the trade name ALIMTA® as a sterile lyophilized powder for intravenous administration.

Formula I

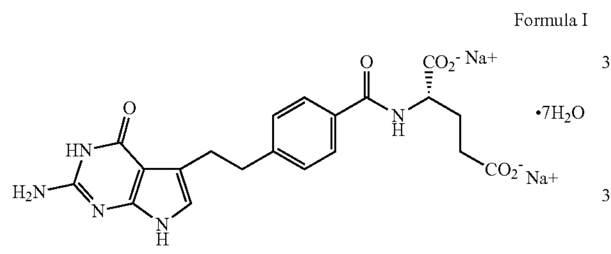

The commercial product is reported to be a lyophilized powder of pemetrexed disodium heptahydrate and mannitol. The commercially available product is supplied as a sterile lyophilized powder for intravenous infusion available in single-dose vials containing 100 mg or 500 mg pemetrexed. The lyophilized product is reconstituted with 0.9% sodium chloride to a concentration of 25 mg/ml, which is further diluted to a concentration of 1 mg/mL to 5 mg/ml before its administration as an intravenous infusion.

U.S. Pat. No. 9,789,113B2 discloses pharmaceutical compositions derived from pemetrexed dipotassium nonahydrate characterized by X-ray powder diffraction pattern containing at least 5 characteristic 2θ° diffraction angle peaks in a lyophilized formulations for injection. The composition discloses 155.73 mg pemetrexed dipotassium nonahydrate (equivalent to 100 mg pemetrexed) with 100 mg mannitol and 778.64 mg pemetrexed dipotassium nonahydrate (equivalent to 500 mg pemetrexed) with 500 mg mannitol. It also discloses a process for manufacturing lyophilized composition having a pH of 7.2 which is achieved by using potassium hydroxide and hydrochloric acid. However, the application fails to discloses the physical and chemical stability data of the composition for long-term at 25° C.

CN105726492 discloses a freeze-dried powder for injection of pemetrexed dipotassium that includes pemetrexed dipotassium, mannitol, and optionally sodium sulphite as an antioxidant. It also discloses a process that generates in-situ pemetrexed dipotassium in composition wherein the process involves mixing a pemetrexed diacid with potassium hydroxide (KOH) solution, adding accessory materials, followed by aseptic filtration and lyophilization. It discloses the use of potassium hydroxide which regulates the pH of the composition between 7 to 8. However, the application fails to disclose physical and chemical stability data for the composition after long-term storage at 25° C.

WO2018002956A1 discloses an injectable solution of pemetrexed comprising pemetrexed disodium heptahydrate, water for injection, a dissolved oxygen content in the range of 0 ppm to 0.2 ppm, wherein the pH is adjusted between 6 to 8 using sodium hydroxide and/or hydrochloric acid. Along with listing steps for achieving the stable solution with low dissolved oxygen content, it also discloses a maximum stability of 1 year having total impurities in the solution not more than 2.0% by weight of pemetrexed.

U.S. Pat. No. 9,421,207B2 discloses a ready-to-use solution or a lyophilized composition comprising pemetrexed in a free acid form and specifically disclosing tromethamine. It also discloses the processes for preparation of the ready-to-use solution formulation or lyophilized pharmaceutical composition of the present invention. Further, it discloses controlling oxygen content with inert gas purging, using chelating agents, amino acids and maintaining higher pH values using pharmaceutically acceptable organic amines is useful in controlling the oxidative and acidic degradation of pemetrexed.

WO200156575 A1 discloses a liquid parenteral composition comprising pemetrexed and at least one antioxidant selected from monothioglycerol, L-cysteine, and thioglycolic acid; and a pharmaceutically acceptable excipient. It further discloses the reparation for the ready to use, liquid solutions of pemetrexed, which includes certain antioxidants, including monothioglycerol, L-cysteine, and thioglycolic acid. The disclosure specifically emphasizes preparing the liquid parenteral composition with the desired characteristics, which is possible only when antioxidant is used, selected from monothioglycerol, L-cysteine, and thioglycolic acid.

CN103784454 discloses a pharmaceutical composition comprising disodium pemetrexed and mannitol, wherein disodium pemetrexed has a crystal structure measured by a powder X-ray diffraction method, represented by a diffraction angle of 2θ±0.2. It also discloses the different mass ratio of disodium pemetrexed to mannitol used in making the composition. The invention specifically discloses the advantage of the new crystalline form of pemetrexed disodium, such as higher bioavailability, easy to store with improved moisture sensitivity.

JP6854710B2 emphasize on a ready to use solution for injection containing pemetrexed or a pharmaceutically acceptable salt thereof and cysteine as an antioxidant, wherein the concentration of the cysteine is 0.3 mg/mL to 2 mg/mL and the pH of the composition is 9.0 or more. An injectable solution formulation containing pemetrexed, which does not contain other antioxidants and does not contain organic solvents. It also discloses the preparation of injectable solution in sealed & closed container having a void or head space oxygen concentration of 1% or less in the container. The art emphasizes more on the use of cysteine, which can suppress the generation of pemetrexed related substances and insoluble foreign substances upon storage.

So, it is well known that pharmaceutical formulations of pemetrexed or its salts are susceptible to degradation over time due to various environmental factors, including but not limited to pH, temperature, humidity, and oxidative conditions. Such degradation can lead to the formation of related impurities or degradants, which may pose potential safety risks to patients and compromise the commercial viability of the product. There exists a continuous need in the pharmaceutical field for a composition of pemetrexed or its pharmaceutically acceptable salts that demonstrates enhanced long-term stability. Such stability is required to ensure that the composition maintains its desired physical and chemical properties throughout the duration of its shelf life. Also, it was observed that the prior art lacked sufficient data to demonstrate a stable, pharmaceutically acceptable and safe pemetrexed dipotassium composition.

The present inventors addressed the unmet need of stable injectable formulation of Pemetrexed Dipotassium by providing the composition of present invention which effectively mitigates the issue with additional advantage of being less cardiotoxic as compared to the sodium salt Accordingly, the present invention relates to a lyophilized pharmaceutical composition comprising pemetrexed in the form of a dipotassium salt, which offers significant advantages over conventional disodium formulations, particularly for patients at risk of cardiovascular conditions by minimizing sodium ion intake and reducing associated risks such as fluid retention and elevated blood pressure. Additionally, the inventors have surprisingly achieved low impurity levels along with enhanced stability using an integrated approach having hydrochloric acid as pH-modifying agent by explicitly excluding the use of hydroxide base pH modifiers and maintaining residual moisture content below 2% throughout the shelf life by employing a highly optimized lyophilization process. This strategic approach not only minimizes degradation but also results in a reconstitutable composition with minimal impurity formation after at least 12 months, after at least 24 months or after at least 36 months at a temperature of 25° C. The formulation prepared is used in the treatment of non-squamous NSCLC or mesothelioma.

As a result, the inventors have been able to design a composition which is capable of resisting the formation of degradation products over an extended storage period, thereby enhancing patient safety and ensuring the commercial feasibility of the product. In particular, the present invention relates to a lyophilized composition of pemetrexed dipotassium that maintains its stability for a period of at least 12 months, 24 months or 36 months when stored under controlled conditions, specifically at a temperature of approximately 25° C. The present inventors conducted certain experiments to develop a desired composition which can meet the expectations of both patients and health care providers.

SUMMARY

In some embodiments, the invention is directed to a reconstitutable lyophilized composition comprising pemetrexed dipotassium, mannitol and a pH modifying component consisting essentially of hydrochloric acid.

In some embodiments, the active ingredient used in the lyophilized composition is pemetrexed dipotassium, wherein the pemetrexed dipotassium is present in form of solvates, hydrates, anhydrates, enantiomers, isomers, polymorphs, or mixture thereof. In some embodiments, the active ingredient is pemetrexed dipotassium, which is either crystalline or amorphous in physical nature. In some embodiments, the active ingredient is pemetrexed dipotassium, which is in hydrate or anhydrate form. In some embodiments, the lyophilized composition has pemetrexed dipotassium in anhydrate form. In another embodiment, the process for manufacturing the lyophilized composition comprises the use of pemetrexed dipotassium heptahydrate.

In another embodiment, the invention is directed to a reconstitutable lyophilized composition comprising pemetrexed dipotassium, mannitol and a pH modifying component consisting essentially of hydrochloric acid; with the proviso that the pH modifying component does not include a hydroxide base.

In some embodiments, the invention is directed to an reconstitutable lyophilized composition comprises pemetrexed dipotassium selected in an amount of about 118.3 mg equivalent to 100 mg of pemetrexed, mannitol in an amount of about 106 mg; or pemetrexed dipotassium in an amount of about 591.5 mg equivalent to 500 mg pemetrexed, mannitol in an amount of about 500 mg, and a pH modifying component consisting essentially of hydrochloric acid; with the proviso that the pH modifying component does not include a hydroxide base, wherein the lyophilized composition has a pH from 6.6 to 7.8 when measured after reconstitution with 0.9% sodium chloride injection or 5% dextrose solution for injection. More preferably, the lyophilized composition has a pH from 6.8 to 7.1, when measured after reconstitution with 0.9% sodium chloride injection or 5% dextrose solution for injection.

The inventors have unexpectedly achieved low impurity levels in the lyophilized pemetrexed dipotassium composition by employing a combination approach of involving the use of hydrochloric acid as the sole pH-modifying component and maintaining residual moisture content below 2% w/w throughout shelf life. This combination significantly reduces degradation, thereby enhancing the stability, extending the shelf life of the composition and making composition reconstitutable, with minimal impurity formation even after storage of at least 12 months, at least 24 months or at least 36 months.

In some embodiments, the invention is directed to a reconstitutable lyophilized composition comprising pemetrexed dipotassium, mannitol and a pH modifying component consisting essentially of hydrochloric acid; with the proviso that the pH modifying component does not include a hydroxide base; wherein after storage for at least 12 months at a temperature of 25° C. in sealed and sterile vial, the composition comprises not more than 0.6% w/w of total impurities as determined by HPLC analysis after said storage condition. In some embodiments, the invention is directed to a reconstitutable lyophilized composition comprising pemetrexed dipotassium, mannitol and a pH modifying component consisting essentially of hydrochloric acid; with the proviso that the pH modifying component does not include a hydroxide base; wherein after storage for at least 24 months or at least 36 months at a temperature of 25° C. in sealed and sterile vial, the composition comprises not more than 1% w/w of total impurities as determined by HPLC analysis after said storage condition.

In further embodiment, the invention is directed to a reconstitutable lyophilized composition comprising pemetrexed dipotassium, mannitol and a pH modifying component consisting essentially of hydrochloric acid; with the proviso that the pH modifying component does not include a hydroxide base, wherein after storage for at least 12 months at a temperature of 25° C. in sealed and sterile vial, the composition comprises not more than 0.6% w/w of total degradation impurities as determined by HPLC analysis after said storage condition. In further embodiment, the invention is directed to a reconstitutable lyophilized composition comprising pemetrexed dipotassium, mannitol and a pH modifying component consisting essentially of hydrochloric acid; with the proviso that the pH modifying component does not include a hydroxide base, wherein after storage for at least 24 months or at least 36 months at a temperature of 25° C. in sealed and sterile vial, the composition comprises not more than 0.6% w/w of total degradation impurities as determined by HPLC analysis after said storage condition.

In some embodiments, the present invention is directed to a reconstitutable lyophilizes composition comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein after storage for at least 12 months at a temperature of 25° C., the composition comprises (a) not more than 0.6% w/w total impurities (b) not more than 2% w/w total water content; and, (c) not more than 0.6% w/w total degradation impurities; wherein the degradation impurities are selected from:

(i) impurity-B in an amount that does not exceed 0.1% w/w;

(ii) impurity-C in an amount that does not exceed 0.1% w/w;

(iii) impurity-E in an amount that does not exceed 0.1% w/w;

(iv) ketopemetrexed in an amount that does not exceed 0.2% w/w; and a combination of two or more thereof.

The present invention provides a process for manufacturing a lyophilized composition of pemetrexed dipotassium using a highly optimized freeze-drying cycle, including an annealing step, to ensure product stability, integrity, and low impurity levels. By employing a tailored freeze-drying process and using hydrochloric acid as the sole pH modifying agent, the inventors have achieved sustained moisture control typically below 2% w/w and remarkably low levels of total impurities not more than 0.6% % w/w, after storage for at least 12 months at 25° C.

In one of the embodiments, the present invention is directed to a reconstitutable lyophilized pharmaceutical composition, comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base wherein the composition is prepared by a process comprising:

(a) dissolving mannitol in water for injection at about 13±3° C. to obtain a clear solution;

(b) adding a portion of the mannitol solution to a container containing pemetrexed dipotassium as pemetrexed dipotassium heptahydrate on anhydrous basis to obtain a slurry;

(c) adding the slurry to the bulk of the mannitol solution and stirring until a clear solution is obtained;

(d) adjusting the pH of the clear solution with hydrochloric acid to about 6.6 to about 7.8;

(e) adjusting the volume of the solution by adding the water for injection to obtain a bulk solution with target drug concentration;

(f) sterilizing the bulk solution using a pre-sterilized 0.22 μm filter;

(g) aseptically transferring the sterile bulk solution to a vial and partially stoppering the vial under nitrogen wherein the bulk solution filed in vial is cooled to about 8° C. for freeze drying, wherein the freeze-drying process comprises;

(1) freezing the bulk solution in a vial in accordance with the following steps sequentially to perform annealing;

(A) exposing the bulk solution obtained from step (g) to a temperature ranging from about −30° C. to about −50° C. and holding it for from about 70 to about 90 minutes;

(B) exposing the product of step (A) to temperature ranging from about −5° C. to about −15° C. and holding it for from about 50 to about 70 minutes;

(C) exposing the product of step (B) to temperature ranging from about −30° C. to about −50° C. and holding it for from about 95 to about 125 minutes;

(2) performing a primary drying of the product obtained of step (1) (C) at a temperature of from about −17° C. to about 25° C.; and (3) performing a secondary drying of product obtained in the step (2) at about 45° C.

(h) completely stoppering the vials after completion of freeze-drying process under filtered nitrogen; and (i) sealing and packing the vial;

wherein after storage for at least 12 months at a temperature of 25° C., the composition in the vial comprises:

(a) not more than 0.6% w/w total impurities;

(b) not more than 2% w/w total water content; and (c) not more than 0.6% w/w total degradation impurities; wherein the degradation impurities are selected from:

(i) impurity-B in an amount that does not exceed 0.1% w/w;

(ii) impurity-C in an amount that does not exceed 0.1% w/w;

(iii) impurity-E in an amount that does not exceed 0.1% w/w;

(iv) ketopemetrexed in an amount that does not exceed 0.2% w/w; and a combination of two or more thereof.

As used herein, the term "portion" means an amount necessary or effective to achieve the result desired. For example, in certain embodiments of the present invention, "portion" refers to the amount of mannitol solution necessary or effective to obtain a slurry of pemetrexed dipotassium.

As used herein, the term "bulk of the mannitol solution" may mean the amount of mannitol solution remaining after the portion of mannitol is added to a container containing pemetrexed dipotassium as pemetrexed dipotassium heptahydrate on anhydrous basis to obtain a slurry.

In some embodiments, the lyophilized composition is provided in sealed and sterile vial.

The present invention relates to a lyophilized pharmaceutical composition comprising pemetrexed in the form of a dipotassium salt, offering added advantages for patients at risk of cardiovascular conditions by minimizing sodium ion intake. Unlike conventional pemetrexed disodium formulations, this composition reduces sodium-associated risks such as fluid retention and elevated blood pressure. The formulation includes mannitol as a bulking agent and hydrochloric acid as the sole pH modifier, explicitly excluding hydroxide bases, and provides a reconstitutable option for treating non-squamous NSCLC or mesothelioma.

In some embodiments, the present provides a method of treating non-squamous NSCLC or mesothelioma to a patient in need thereof comprises administering of (i) a reconstitutable lyophilized pharmaceutical composition comprises pemetrexed dipotassium selected in an amount of about 118.3 mg equivalent to 100 mg of pemetrexed and mannitol in an amount of about 106 mg or (ii) pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base; wherein after at least 12 months at a temperature of 25° C., the composition comprises:

- (a) not more than 0.6% w/w total impurities;
- (b) not more than 2% w/w total water content; and
- (c) not more than 0.6% w/w total degradation impurities; wherein the degradation impurities are selected from:
  - (i) impurity-B in an amount that does not exceed 0.1% w/w;
  - (ii) impurity-C in an amount that does not exceed 0.1% w/w;
  - (iii) impurity-E in an amount that does not exceed 0.1% w/w;
  - (iv) ketopemetrexed in an amount that does not exceed 0.2% w/w; and a combination of two or more thereof.

In further embodiment, the invention is directed to a method of treating non-squamous NSCLC or mesothelioma to a patient in need thereof comprises administration of a reconstitutable lyophilized composition of invention, wherein the lyophilized composition is reconstituted in less than 70 seconds with 0.9% sodium chloride solution for injection or 5% dextrose solution for injection.

In some embodiments, the present provides a method of treating non-squamous NSCLC or mesothelioma to a patient in need thereof comprises administration of a reconstitutable lyophilized pharmaceutical composition comprises pemetrexed dipotassium, mannitol in an amount and a pH modifying component consisting essentially of hydrochloric acid; with the proviso that the pH modifying component does not include a hydroxide base, wherein the salt form of the pharmaceutically active agent in the composition is selected as non-sodium salt to avoid or reduce the administration of sodium ions to the patient.

DETAILED DESCRIPTION OF INVENTION

As used in the specification and the appended claims, the singular forms of "a," "an" and "the" include plural references unless the context clearly dictates otherwise.

As used herein, the "about" term refers to the deviation of ±5% from the said value. For example, about 118.3 mg encompasses both the values as 118.3+5% and 118.3−5%.

As used herein, the term "Pemetrexed dipotassium" includes solvates, hydrates, anhydrates, enantiomers, isomers, polymorphs, or mixture thereof. In some embodiments, the active ingredient is pemetrexed dipotassium, which is either crystalline or amorphous in physical form. In some embodiments, the active ingredient is pemetrexed dipotassium, which is in hydrate or anhydrate form. In some embodiments, the lyophilized composition includes pemetrexed dipotassium in anhydrate form. In some embodiments, the process for manufacturing the lyophilized composition comprises the use of pemetrexed dipotassium heptahydrate.

As used herein, the "pH modifying component" refers to an ingredient or combination of ingredients present in an amount effective to modify or adjust the pH of the composition to a desired pH, which is added during the process of manufacturing composition prior to lyophilization. As an example, the excipient which can act as pH modifier to composition includes acidifying agent and alkalizing agent. The acidifying agent includes, but are not limited to, known mineral acids (e.g., hydrochloric acid, sulfuric acid, phosphoric acid) and organic acids (e.g., citric acid, lactic acid, acetic acid, ascorbic acid). Alkalizing agents include hydroxide bases such as sodium hydroxide and potassium hydroxide. In preferred embodiment, the present invention is directed to the lyophilized composition which has a pH modifying component consisting essentially of hydrochloric acid; with the proviso that the pH modifying component does not include a hydroxide base.

As used herein, the "reconstitutable" refers to rapid formation of clear solution upon the addition of a reconstitution medium selected from 0.9% saline solution for injection or 5% dextrose solution for injection to the lyophilized composition of pemetrexed dipotassium in a designated time prior to administration. It is characterized by complete solubility, leaving no visible particles or residue, and must maintain the safety, efficacy, and integrity of the active pharmaceutical ingredient after reconstitution. Upon reconstitution, the composition should dissolve quickly, typically within a few seconds to few minutes with minimal shaking or agitation. In some embodiments, the reconstitutable composition requires less than 90 seconds, preferably, less than 80 seconds more preferably, less than 70 seconds as reconstitution time to become clear solution upon addition of reconstitution medium. In a preferred embodiment, a reconstitutable lyophilized composition is the composition which requires less than 70 seconds as reconstitution time to become clear solution upon addition of reconstitution medium.

As used herein, the term "stable" or "stability" or "stabilized" refers to physical and chemical stability of composition upon storage for a specific time and condition. In some embodiments of the invention, stability after storage for at least 12 months at a temperature of 25° C. refers to the long-term stability of the lyophilized composition of pemetrexed dipotassium. In another embodiment, stability after storage for at least 24 months at a temperature of 25° C. also refers to the long-term stability of the lyophilized composition of pemetrexed dipotassium. In another embodiment, the current lyophilized composition was subjected to stability studies beyond the shelf life period of 24 months to about 36 months and was found to be stable, meeting both physical and chemical parameters as desired. In another embodiment, stability after storage for at least 36 months at a temperature of 25° C. also refers to the long-term stability of the lyophilized composition of pemetrexed dipotassium. It is to be understood that, throughout the specification disclosed, the storage condition of 25° C. means 25° C.±2° C. and relative humidity of 60%±5% RH, which is as per the international regulatory guidelines representing room temperature storage of drug product in a pharmacy/hospital shelf. In another embodiment, the stability at 2-8° C. for 24 hours refers to the stability of reconstituted solution of the lyophilized composition of pemetrexed dipotassium after reconstitution with reconstitution medium. In further embodiment, the stability of the composition is measured by evaluating physical and chemical quality parameters like, reconstitution time, impurities such as impurity-B, impurity- C, impurity-E, ketopemetrexed, total impurities % w/w, total degradation impurities % w/w, assay and water content % w/w.

As used herein, the term "relative humidity (RH)" refers in the context of pharmaceutical stability testing, defined as the percentage of moisture in the air relative to the maximum amount the air can hold at a given temperature. It is a key environmental parameter used in stability studies to assess how a drug product responds to different humidity conditions over time. Controlled RH levels (e.g., 60% RH at 25° C. for long-term, 75% RH at 40° C. for accelerated testing) are used during storage to simulate storage conditions and evaluate the product's physical, chemical, and microbiological stability, ensuring it remains safe and effective throughout its shelf life.

As used herein, the "total impurities" refers to summation of all known, unknown and degradation impurities of lyophilized composition of pemetrexed dipotassium after storage for at least 12 months, at least 24 months or at least 36 months in a sealed and sterile vial at a temperature of 25° C.

As used herein, the term "degradation impurity" refers to any compound resulting from the chemical degradation of pemetrexed. Exemplary degradation pathways include but are not limited to amide and/or hydrolysis, oxidation, epimerization, and other degradation pathways which include oxidation by free radicals, reactions with other molecules, or changes in pH. In some embodiments, the total degradation impurities are selected from impurity-B, impurity-C, impurity-E, ketopemetrexed and a combination of two or more thereof generated after storage for at least 12 months, at least 24 months or at least 36 months.

As used herein, the "annealing" refers to a controlled thermal treatment in a freeze-drying process, used between initial freezing and primary drying to optimize product structure and improve freeze-drying efficiency, leading to a higher-quality and more stable lyophilized product. In some embodiments, the process of freeze-drying comprises annealing process which is performed after initial cooling but before primary drying. In some embodiments, after the initial cooling, the product temperature is further reduced to induce freezing followed by thawing the product before again freezing it finally to induce annealing and held for a specified period, before resuming primary drying.

As used herein, the term "free from particulate matter" refers to a composition solution that is substantially free and does not contain visible or detectable solid particles, aggregates, or insoluble matter when evaluated using standard visual inspection or analytical techniques which is appropriate and acceptable by regulatory authority.

In some embodiments, the lyophilized composition comprises a bulking agent selected from the group consisting of mannitol, lactose, sucrose, dextrose, and glycine. The bulking agent serves to increase the solid content of the formulation, thereby facilitating handling, lyophilization, and accurate dosing. In particular embodiments, mannitol is preferred as a bulking agent.

In some embodiments, the drug substance used to manufacture the lyophilized composition is pemetrexed dipotassium heptahydrate. Pemetrexed dipotassium heptahydrate, which has the chemical name L-glutamic acid, N-[4-[2-(2-amino-4,7-dihydro-4-oxo-1H-pyrrolo[2,3-d]pyrimidin-5-yl) ethyl]benzoyl]-, dipotassium salt, heptahydrate. It is a white to off-white powder with a molecular formula of $C_{20}H_{19}K_2N_5O_6 \cdot 7H_2O$ and a molecular weight of 629.49. The structural formula of pemetrexed dipotassium heptahydrate is as follows:

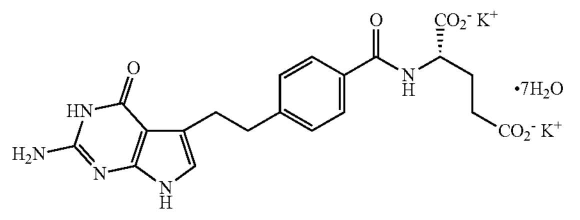

Based on molecular weight 139.4 mg pemetrexed dipotassium heptahydrate is equivalent to 100 mg pemetrexed on an anhydrous basis and 696.9 mg of pemetrexed dipotassium heptahydrate is equivalent to 500 mg pemetrexed on an anhydrous basis.

In some embodiments, the present invention is directed to lyophilized composition comprising pemetrexed dipotassium and mannitol. The composition for Injection is supplied as a sterile white to light-yellow or green-yellow lyophilized powder or cake for intravenous infusion available in single-dose vials. The molecular weight of pemetrexed dipotassium is 503.59 g/mol as shown in formula II.

Formula II

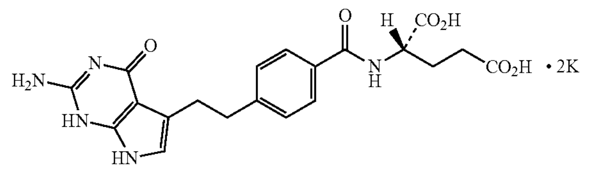

Based on molecular weight 118.3 mg of pemetrexed dipotassium is equivalent to 100 mg pemetrexed on anhydrous basis and 591.5 mg of pemetrexed dipotassium heptahydrate is equivalent to 500 mg pemetrexed on anhydrous basis.

In some embodiments, the invention is directed to a reconstitutable lyophilized composition comprising pemetrexed dipotassium in an amount selected from about 118.3 mg to about 591.5 mg equivalent to about 100 mg to about 500 mg of pemetrexed, mannitol in an amount selected from about 106 mg to about 500 mg and a pH modifying component consisting essentially of hydrochloric acid; with the proviso that the pH modifying component does not include a hydroxide base. In particular embodiment, the present invention provides a lyophilized composition comprises pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg.

In some embodiments, the invention is directed to a reconstitutable lyophilized composition comprises pemetrexed dipotassium selected in an amount of about 118.3 mg equivalent to 100 mg of pemetrexed, mannitol in an amount of about 106 mg; or pemetrexed dipotassium in an amount of about 591.5 mg equivalent to 500 mg pemetrexed, mannitol in an amount of about 505 mg and a pH modifying component consisting essentially of hydrochloric acid; with the proviso that the pH modifying component does not include a hydroxide base, wherein the lyophilized composition has a pH from 6.6 to 7.8, when measured after reconstitution with 0.9% sodium chloride injection or 5% dextrose solution for injection. In a preferred embodiment, the lyophilized composition has a pH from 6.8 to 7.1, when measured after reconstitution with 0.9% sodium chloride injection or 5% dextrose solution for injection.

In some embodiments, the invention is directed to a reconstitutable lyophilized composition comprises pemetrexed dipotassium selected in an amount of about 118.3 mg equivalent to 100 mg of pemetrexed, mannitol in an amount of about 106 mg; or pemetrexed dipotassium in an amount of about 591.5 mg equivalent to 500 mg pemetrexed, mannitol in an amount of about 500 mg, and a pH modifying component consisting essentially of hydrochloric acid; with the proviso that the pH modifying component does not include a hydroxide base, wherein the lyophilized composition has a pH from 6.6 to 7.8, when measured after reconstitution with 0.9% sodium chloride injection or 5% dextrose solution for injection, wherein the reconstitution time of the lyophilized composition is less than about 70 seconds, when reconstituted with the aqueous solvent selected from the group consisting of 0.9% sodium chloride solution for injection or 5% dextrose solution for injection. In a preferred embodiment, the lyophilized composition has a pH from 6.8 to 7.1, when measured after reconstitution with 0.9% sodium chloride injection or 5% dextrose solution for injection.

In some embodiments, the invention is directed to a reconstitutable lyophilized composition comprises pemetrexed dipotassium selected in an amount of about 118.3 mg equivalent to 100 mg of pemetrexed, mannitol in an amount of about 106 mg; or pemetrexed dipotassium in an amount of about 591.5 mg equivalent to 500 mg pemetrexed, mannitol in an amount of about 500 mg, and a pH modifying component consisting essentially of hydrochloric acid; with the proviso that the pH modifying component does not include a hydroxide base, wherein the lyophilized composition has a pH from 6.6 to 7.8, when measured after reconstitution with 0.9% sodium chloride injection or 5% dextrose solution for injection, wherein the reconstituted solution is free from particulate matter and stable at 2-8° C. for 24 hours from the time of reconstitution. In a preferred embodiment, the lyophilized composition has a pH from 6.6 to 7.8, when measured after reconstitution with 0.9% sodium chloride injection or 5% dextrose solution for injection.

In some embodiments, the invention is directed to a reconstitutable lyophilized composition comprises pemetrexed dipotassium selected in an amount of about 118.3 mg equivalent to 100 mg of pemetrexed, mannitol in an amount of about 106 mg; or pemetrexed dipotassium in an amount of about 591.5 mg equivalent to 500 mg pemetrexed, mannitol in an amount of about 500 mg, and a pH modifying component consisting essentially of hydrochloric acid; with the proviso that the pH modifying component does not include a hydroxide base, wherein the composition remains stable after storage for at least 12 months in sealed and sterile vial at a temperature of 25° C. In further embodiment, the lyophilized composition remains stable after storage for at least 24 months in sealed and sterile vial at a temperature of 25° C. In further embodiment, the lyophilized composition remains stable after storage for at least 36 months in sealed and sterile vial at a temperature of 25° C. In further embodiment, the lyophilized composition has a pH from 6.6 to 7.8, when measured after reconstitution with 0.9% sodium chloride injection or 5% dextrose solution for injection. In a preferred embodiment, the lyophilized composition has a pH from 6.8 to 7.1, when measured after reconstitution with 0.9% sodium chloride injection or 5% dextrose solution for injection.

In some embodiments, the present invention is directed at a reconstitutable lyophilized composition comprising pemetrexed dipotassium, mannitol and a pH modifying component consisting essentially of hydrochloric acid; with the proviso that the pH modifying component does not include a hydroxide base, wherein the composition remains stable physically as well as chemically after storage for at least 12 months, at least 24 months or at least 36 months at a temperature of 25° C.

The lyophilized composition having sensitive molecule like pemetrexed dipotassium, which can be stored without significant loss of potency or structural integrity while ensuring that the drug remains effective and safe to use even after months or years of manufacturing is a challenging aspect. In essence, long-term stability is key to patient safety, maintaining product quality, regulatory compliance and commercial viability throughout the product's intended shelf life. Among the several factors responsible for a long term stability, controlling the pH range and moisture content of the pharmaceutical composition are especially critical. Typically, pH adjustment during formulation preparation involves use of both acidifying and alkalizing agents, which may expose the drug substance to a wide pH range during formulation. Such exposure can increase the risk of degradation or impurity formation. Therefore, it is advantageous, although technically challenging, to achieve the target pH using a single pH modifying component. In addition, moisture content is a critical determinant of product stability. Excess moisture can accelerate degradation reactions such as hydrolysis, compromise the structural integrity of the cake, reduce the shelf life of the drug, and may lead to changes in reconstitution time. Therefore, controlling residual moisture within strict limits is essential.

The inventors have surprisingly found very low levels of impurity generation in the composition, through a strategic approach of combination of using only hydrochloric acid as a single pH modifying component to achieve the desired pH and stricter control of the moisture/water content of the composition throughout shelf life. The use of a single pH modifying component in preparing pemetrexed dipotassium compositions of the invention plays a significant role in reducing the degradation of pemetrexed thereby prolonging the shelf-life of said pemetrexed compositions. Also, substantial control of water/moisture content typically not more than 1% w/w during manufacture and not more than 2% w/w, during the storage has given surprising leverage with low levels of impurity even after storage for at least 12 months, at 25° C.

In some embodiments, the present invention is directed to a reconstitutable lyophilizes composition comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and

- a pH modifying component consisting essentially of hydrochloric acid; with the proviso that the pH modifying component does not include a hydroxide base, wherein after storage for at least 12 months at a temperature of 25° C., the composition comprises:

(a) not more than 1.2% w/w total impurities;

(b) not more than 3% w/w total water content; and (c) not more than 1.1% w/w total degradation impurities; wherein the degradation impurities are selected from:

(i) impurity-B in an amount that does not exceed 0.15% w/w;

(ii) impurity-C in an amount that does not exceed 0.15% w/w;

(iii) impurity-E in an amount that does not exceed 0.15% w/w;

(iv) ketopemetrexed in an amount that does not exceed 0.6% w/w; and a combination of two or more thereof.

In further embodiment, the lyophilized composition has a pH from 6.6 to 7.8, when measured after reconstitution with 0.9% sodium chloride injection or 5% dextrose solution for injection. In a preferred embodiment, the lyophilized composition has a pH from 6.8 to 7.1, when measured after reconstitution with 0.9% sodium chloride injection or 5% dextrose solution for injection. In some embodiments, the reconstitution time of the lyophilized composition is less than about 70 seconds, when reconstituted with the aqueous solvent selected from the group consisting of 0.9% sodium chloride solution for injection or 5% dextrose solution for injection. In one of the embodiments described above, the storage period of the lyophilized composition is at least 24 months or at least 36 months at a temperature of 25° C.

In some embodiments, the present invention is directed to a reconstitutable lyophilizes composition comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein after storage for at least 12 months at a temperature of 25° C., the composition comprises:

(a) not more than 0.6% w/w total impurities;

(b) not more than 2% w/w total water content; and (c) not more than 0.6% w/w total degradation impurities; wherein the degradation impurities are selected from:

(i) impurity-B in an amount that does not exceed 0.1% w/w;

(ii) impurity-C in an amount that does not exceed 0.1% w/w;

(iii) impurity-E in an amount that does not exceed 0.1% w/w;

(iv) ketopemetrexed in an amount that does not exceed 0.2% w/w; and a combination of two or more thereof.

In further embodiment, the lyophilized composition has a pH from 6.6 to 7.8, when measured after reconstitution with 0.9% sodium chloride injection or 5% dextrose solution for injection. In a preferred embodiment, the lyophilized composition has a pH from 6.8 to 7.1, when measured after reconstitution with 0.9% sodium chloride injection or 5% dextrose solution for injection. In some embodiments, the reconstitution time of the lyophilized composition is less than about 70 seconds, when reconstituted with the aqueous solvent selected from the group consisting of 0.9% sodium chloride solution for injection or 5% dextrose solution for injection.

In some embodiments, the present invention is directed to a reconstitutable lyophilizes composition comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein the wherein after storage for at least 12 months at a temperature of 25° C., the composition comprises:

(a) not more than 0.6% w/w total impurities;

(b) not more than 2% w/w total water content; and (c) not more than 0.6% w/w total degradation impurities; wherein the degradation impurities are selected from:

(i) impurity-B in an amount that does not exceed 0.05% w/w;

(ii) impurity-C in an amount that does not exceed 0.05% w/w;

(iii) impurity-E in an amount that does not exceed 0.04% w/w;

(iv) ketopemetrexed in an amount that does not exceed 0.15% w/w; and a combination of two or more thereof.

In further embodiment, the lyophilized composition has a pH from 6.6 to 7.8, when measured after reconstitution with 0.9% sodium chloride injection or 5% dextrose solution for injection. In a preferred embodiment, the lyophilized composition has a pH from 6.8 to 7.1, when measured after reconstitution with 0.9% sodium chloride injection or 5% dextrose solution for injection. In some embodiments, the reconstitution time of the lyophilized composition is less than about 70 seconds, when reconstituted with the aqueous solvent selected from the group consisting of 0.9% sodium chloride solution for injection or 5% dextrose solution for injection.

In some embodiments, the present invention is directed to a reconstitutable lyophilizes composition comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein after storage for at least 24 months at a temperature of 25° C., the composition comprises:

(a) not more than 1% w/w total impurities;

(b) not more than 2% w/w total water content; and (c) not more than 0.6% w/w total degradation impurities; wherein the degradation impurities are selected from:

(i) impurity-B in an amount that does not exceed 0.1% w/w;

(ii) impurity-C in an amount that does not exceed 0.1% w/w;

(iii) impurity-E in an amount that does not exceed 0.1% w/w;

(iv) ketopemetrexed in an amount that does not exceed 0.2% w/w; and a combination of two or more thereof.

In further embodiments, the lyophilized composition has a pH from 6.6 to 7.8, when measured after reconstitution with 0.9% sodium chloride injection or 5% dextrose solution for injection. In a preferred embodiment, the lyophilized composition has a pH from 6.8 to 7.1, when measured after reconstitution with 0.9% sodium chloride injection or 5% dextrose solution for injection. In some embodiments, the reconstitution time of the lyophilized composition is less than about 70 seconds, when reconstituted with the aqueous solvent selected from the group consisting of 0.9% sodium chloride solution for injection or 5% dextrose solution for injection. In one of the embodiments described herein, the storage period of the lyophilized composition is at least 36 months at a temperature of 25° C.

In some embodiments, the present invention is directed to a reconstitutable lyophilizes composition comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein the wherein after storage for at least 24 months at a temperature of 25° C., the composition comprises:

(a) not more than 1% w/w total impurities;

(b) not more than 2% w/w total water content; and (c) not more than 0.6% w/w total degradation impurities; wherein the degradation impurities are selected from:

(i) impurity-B in an amount that does not exceed 0.05% w/w;

(ii) impurity-C in an amount that does not exceed 0.05% w/w;

(iii) impurity-E in an amount that does not exceed 0.04% w/w;

(iv) ketopemetrexed in an amount that does not exceed 0.15% w/w; and a combination of two or more thereof.

In further embodiments, the lyophilized composition has a pH from 6.6 to 7.8, when measured after reconstitution with 0.9% sodium chloride injection or 5% dextrose solution for injection. In a preferred embodiment, the lyophilized composition has a pH from 6.8 to 7.1, when measured after reconstitution with 0.9% sodium chloride injection or 5% dextrose solution for injection. In some embodiments, the reconstitution time of the lyophilized composition is less than about 70 seconds, when reconstituted with the aqueous solvent selected from the group consisting of 0.9% sodium chloride solution for injection or 5% dextrose solution for injection. In one of the embodiments described above, the storage period of the lyophilized composition is at least 36 months at a temperature of 25° C.

In some embodiments, the pH of the lyophilized composition after storage for at least 12 months in a sealed and sterile vial at a temperature of 25° C. is between the range of 6.8 to 7.1. In some embodiments, the pH of the lyophilized composition after storage for at least 24 months in a sealed and sterile vial at a temperature of 25° C. is between the range of 6.8 to 7.1. In some embodiments, the pH of the lyophilized composition after storage for at least 36 months in a sealed and sterile vial at a temperature of 25° C. is between the range of 6.8 to 7.1.

In some embodiments, the present invention provides the lyophilized composition, wherein the total impurities in the composition are not more than 1% w/w, after storage for at least 12 months, at least 24 months or at least 36 months in a sealed and sterile vial at a temperature of 25° C. when analyzed by HPLC. In some embodiments, the present invention provides the lyophilized composition, wherein the total impurities in the composition are selected from the group consisting of not more than 1% w/w, not more than 0.9% w/w, not more than 0.8% w/w, not more than 0.7% or not more than 0.6% w/w after storage for at least 12 months, at least 24 months or at least 36 months in a sealed and sterile vial at a temperature of 25° C. when analyzed by HPLC.

In some embodiments, the present invention is directed to the lyophilized composition, wherein the water content in the composition is not more than 2% w/w, after storage for at least 12 months, at least 24 months or at least 36 months in a sealed and sterile vial at a temperature of 25° C. In some embodiments, the present invention is directed to the lyophilized composition, wherein the water content in the composition is selected from the group consisting of not more than 2% w/w, not more than 1.9% w/w, not more than 1.8% w/w, or not more than 1.7% w/w, after storage for at least 12 months, at least 24 months or at least 36 months in a sealed and sterile vial at a temperature of 25° C. In some embodiments, the water/moisture content is typically less than 1% w/w during manufacture or at the time of batch release and not more than 2% w/w after storage for at least 12 months, at least 24 months or at least 36 months in a sealed and sterile vial at a temperature of 25° C. In some embodiments, the water content in the lyophilized composition is measured by Kal Fischer method known in the art.

In some embodiments, the present invention provides the lyophilized composition, wherein the total degradation impurities in the composition does not exceed 1% w/w, after storage for at least 12 months, at least 24 months or at least 36 months in a sealed and sterile vial at a temperature of 25° C. when analyzed by HPLC. In some embodiments, the present invention provides the lyophilized composition, wherein the total degradation impurities in the composition does not exceed the value selected from the group consisting of 1% w/w, 0.9% w/w, 0.8% w/w, 0.7% w/w, 0.6% w/w, 0.5% w/w, 0.4% w/w or 0.3% w/w, after storage for at least 12 months, at least 24 months or at least 36 months in a sealed and sterile vial at a temperature of 25° C. when analyzed by HPLC.

Certain compounds have been identified as impurities stemming from pemetrexed degradation as shown in Table 1 (below). In some embodiments, the degradation impurities are measured by HPLC method.

TABLE 1

| Probable degradation impurities of stemming from pemetrexed degradation in a long-term stability study | | | |
|---|---|---|---|
| Impurity name | Chemical Name | Chemical Structure | Source/ mechanism |
| Impurity-B | (2S,2'S)-2,2'-[[(5R)-2,2'-diamino-4,4',6-trioxo-1,4,4',6,7,7'-hexahydro-1'H-5H-5,6'-bipyrrolo[2,3-d] pyrimidine-5,5'-diyl]bis (ethylene-benzene-4,1 diylcarbonyl-imino) dipentanedioic acid | 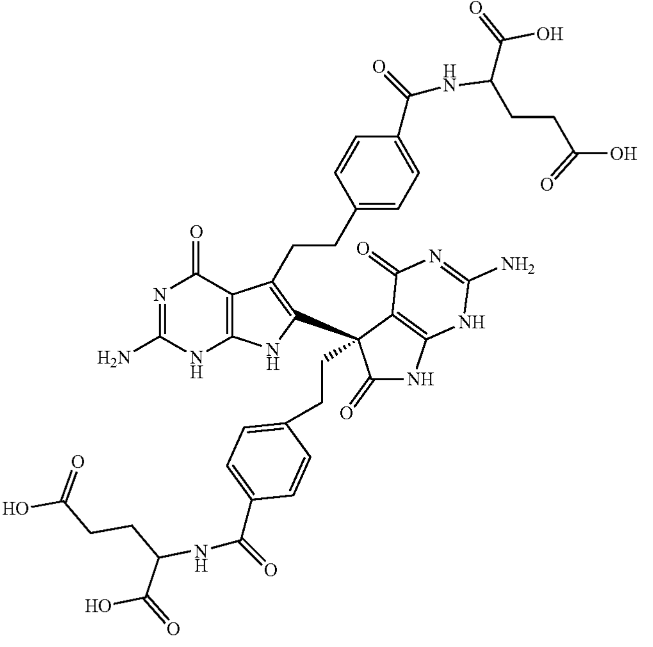 [SMILES: Nc1nc(=O)c2c([nH]1)NC(=O)[C@@]2(CCc1ccc(C(=O)NC(CCC(=O)O)C(=O)O)cc1)c1[nH]c2[nH]c(N)nc(=O)c2c1CCc1ccc(C(=O)NC(CCC(=O)O)C(=O)O)cc1] | Degra-dation product |
| Impurity-C | (2S,2'S)-2,2'-[[(5S)-2,2'-diamino-4,4',6-trioxo-1,4,4',6,7,7'-hexahydro-1'H,5H-5,6' bipyrrolo[2,3-d] pyrimidine-5,5'-diyl]bis (ethylenebenzen-4,1-diylcarbonyl imino)] dipentanedioic acid | 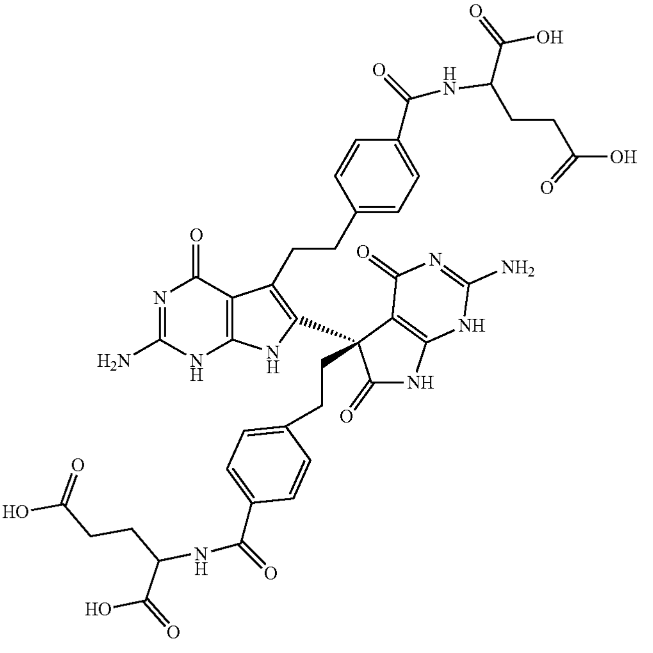 [SMILES: Nc1nc(=O)c2c([nH]1)NC(=O)[C@]2(CCc1ccc(C(=O)NC(CCC(=O)O)C(=O)O)cc1)c1[nH]c2[nH]c(N)nc(=O)c2c1CCc1ccc(C(=O)NC(CCC(=O)O)C(=O)O)cc1] | Degra-dation product |
| Impurity-E | 4-[2-(2-Amino-4-oxo-4,7-dihydro-1H-pyrrolo[2,3-d] pyrimidin-5-yl)-ethyl]-benzoic acid | 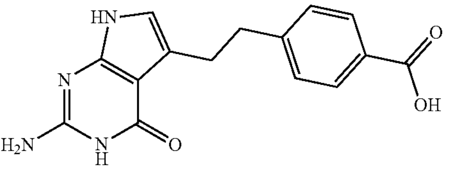 [SMILES: Nc1nc2[nH]cc(CCc3ccc(C(=O)O)cc3)c2c(=O)[nH]1] | Degra-dation product |

TABLE 1-continued

| Probable degradation impurities of stemming from pemetrexed degradation in a long-term stability study | | | |
|---|---|---|---|
| Impurity name | Chemical Name | Chemical Structure | Source/ mechanism |
| Keto-pemetrexed | (4-{2-[(RS)-2-Amino-4,6-dioxo-4,5,6,7-tetrahydro-3H-pyrrolo[2,3-d] pyrimidin-5-ylethyl} benzoyl)-L-glutamic acid | 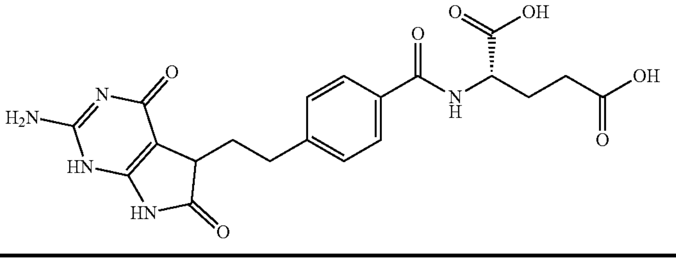 | Degradation degradant |

In some embodiments, the present invention provides the lyophilized composition, wherein the impurity-B in the composition does not exceed 0.1% w/w, after storage for at least 12 months, at least 24 months or at least 36 months in a sealed and sterile vial at a temperature of 25° C. when analyzed by HPLC. In some embodiments, the present invention provides the lyophilized composition, wherein the impurity-B in the composition does not exceed the value selected from the group consisting of 0.1% w/w, 0.09% w/w, 0.08% w/w, 0.07% w/w, 0.06% w/w, 0.05% w/w, or 0.04% w/wafter storage for at least 12 months, at least 24 months or at least 36 months in a sealed and sterile vial at a temperature of 25° C. when analyzed by HPLC.

In some embodiments, the present invention provides the lyophilized composition, wherein the impurity-C in the composition does not exceed 0.1% w/w after storage for at least 12 months, at least 24 months or at least 36 months in a sealed and sterile vial at a temperature of 25° C. when analyzed by HPLC. In some embodiments, the present invention provides the lyophilized composition, wherein the impurity-C in the composition does not exceed the value selected from the group consisting of 0.1% w/w, 0.09% w/w, 0.08% w/w, 0.07% w/w, 0.06% w/w, 0.05% w/w, or 0.04% w/w after storage for at least 12 months, at least 24 months or at least 36 months in a sealed and sterile vial at a temperature of 25° C. when analyzed by HPLC.

In some embodiments, the present invention provides the lyophilized composition, wherein the impurity-E in the composition does not exceed 0.1% w/w after storage for at least 12 months, at least 24 months or at least 36 months in a sealed and sterile vial at a temperature of 25° C. when analyzed by HPLC. In some embodiments, the present invention provides the lyophilized composition, wherein the impurity-E in the composition does not exceed the value selected from the group consisting of 0.1% w/w, 0.09% w/w, 0.08% w/w, 0.07% w/w, 0.06% w/w, 0.05% w/w, or 0.04% w/w after storage for at least 12 months, at least 24 months or at least 36 months in a sealed and sterile vial at a temperature of 25° C. when analyzed by HPLC.

In some embodiments, the ketopemetrexed is a degradation impurity, whose allowed limit as per the US monograph is 0.60% w/w. However, surprisingly the present invention provides very negligible amount of ketopemetrexed generated in the lyophilized composition after storage for at least 12 months, at least 24 months or at least 36 months in a sealed and sterile vial at a temperature of 25° C., which is about less than 66% than the allowed limit by regulatory authority. In some embodiments, the present invention provides the lyophilized composition, wherein the ketopemetrexed in the composition does not exceed 0.2% w/w after storage for at least 12 months, at least 24 months or at least 36 months in a sealed and sterile vial at a temperature of 25° C. when analyzed by HPLC. In some embodiments, the present invention provides the lyophilized composition, wherein the ketopemetrexed in the composition does not exceed the value selected from the group consisting of 0.2% w/w, 0.19% w/w, 0.18% w/w, 0.17% w/w, 0.16% w/w, 0.15% w/w, 0.14% w/w, 0.13% w/w, 0.12% w/w or 0.11% w/w after storage for at least 12 months, at least 24 months or at least 36 months in a sealed and sterile vial at a temperature of 25° C. when analyzed by HPLC.

In some embodiments, the present invention provides the lyophilized composition, wherein the impurity-G in the composition does not exceed 0.1% w/w, after storage for at least 12 months, at least 24 months or at least 36 months in a sealed and sterile vial at a temperature of 25° C. when analyzed by HPLC. In some embodiments, the present invention provides the lyophilized composition, wherein the impurity-G in the composition does not exceed 0.05% w/w, after storage for 24 months or 36 months in a sealed and sterile vial at a temperature of 25° C. when analyzed by HPLC. Impurity-G is a chiral impurity having chemical name as (2R)-2-[[4-[2-(2-amino-4-oxo-4,7-dihydro-1-]H-pyrrolo[2,3-d] pyrimidin-5-yl)ethyl]benzoyl]amino] pentanedioic acid.

In some embodiments, the present invention provides the lyophilized composition, wherein the single specified impurity in the composition does not exceed 0.1% w/w, after storage for at least 12 months, at least 24 months or at least 36 months in a sealed and sterile vial at a temperature of 25° C., when analyzed by HPLC.

In some embodiments, the present invention provides the lyophilized composition, wherein the single unspecified impurity in the composition does not exceed 0.2% w/w, after storage for at least 12 months, at least 24 months or at least 36 months in a sealed and sterile vial at a temperature of 25° C., when analyzed by HPLC.

In some embodiments, the present invention is directed to a reconstitutable lyophilizes composition comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein after storage for at least 12 months at a temperature of 25° C., the composition in the vial comprises:

(a) total impurities selected from the group consisting of not more than 1% w/w, not more than 0.9% w/w, not more than 0.8%, not more than 0.7% w/w or not more than 0.6% w/w (b)) wherein the water content is selected from the group consisting of not more than 2% w/w, not more than 1.9% w/w, not more than 1.8% w/w, or not more than 1.7% w/w, (c) the total degradation impurities selected from the group consisting of not more than 1% w/w, not more than 0.9% w/w, not more than 0.8% w/w, not more than 0.7% w/w, or not more than 0.6% w/w, wherein the degradation impurities are selected from;

(i) impurity-B in an amount that does not exceed the value selected from the group consisting of 0.1% w/w, 0.09% w/w, 0.08% w/w, 0.07% w/w, 0.06% w/w, 0.05% w/w, or 0.04% w/w;

(ii) impurity-C in an amount that does not exceed the value selected from the group consisting of 0.1% w/w, 0.09% w/w, 0.08% w/w, 0.07% w/w, 0.06% w/w, 0.05% w/w, or 0.04%;

(iii) impurity-E in an amount that does not exceed the value selected from the group consisting of 0.1% w/w, 0.09% w/w, 0.08% w/w, 0.07% w/w, 0.06% w/w, 0.05% w/w, or 0.04%;

(iv) ketopemetrexed in an amount that does not exceed the value selected from the group consisting of 0.2% w/w, 0.19% w/w, 0.18% w/w, 0.17% w/w, 0.16% w/w, 0.15% w/w, 0.14% w/w, 0.13% w/w, 0.12% w/w or 0.11% w/w, and a combination of two or more thereof.

In some embodiments, the storage period of the lyophilized composition can be at least 24 months or at least 36 months at a temperature of 25° C. In further embodiments, the lyophilized composition has a pH from 6.6 to 7.8, when measured after reconstitution with 0.9% sodium chloride injection or 5% dextrose solution for injection. In other embodiments, the lyophilized composition has a pH from 6.8 to 7.1, when measured after reconstitution with 0.9% sodium chloride injection or 5% dextrose solution for injection. In some embodiments, the reconstitution time of the lyophilized composition is less than about 70 seconds, when reconstituted with the aqueous solvent selected from the group consisting of 0.9% sodium chloride solution for injection or 5% dextrose solution for injection.

The term "headspace oxygen" as used herein refers to the volume fraction of molecular oxygen present in the gas phase above the lyophilized powder within a sealed container. Minimizing the oxygen content in the headspace is critical for enhancing the oxidative stability of pemetrexed, thereby improving the shelf-life and overall quality of the formulation.

The low headspace oxygen levels of the invention may be achieved through processes such as nitrogen purging, vacuum stoppering, or inert gas overlay techniques during the filling and sealing operations. Headspace oxygen concentration may be determined by methods well known in art.

In some embodiments, the present invention provides the process of manufacturing the lyophilized composition comprising pemetrexed dipotassium, mannitol and hydrochloric acid as a pH modifier, with proviso that the composition does not make use of hydroxide base as pH modifier, wherein the composition is filled into a container having a headspace oxygen concentration of about 3.0% or less. In certain embodiments, the lyophilized composition comprises a headspace oxygen concentration of 2% or less. In further embodiments, the lyophilized composition comprises headspace oxygen concentration 1% or less.

In some embodiments, the present invention provides the process for manufacturing lyophilized composition of pemetrexed dipotassium, which includes freeze-drying or lyophilization. Designing the freeze-drying process is a critical step in ensuring product stability, integrity, and effectiveness. Although lyophilization may appear to be a straightforward dehydration process, but a non-optimized freeze-drying cycle often results in incomplete drying leading to higher water content, poor cake structure, product collapse, or generation of degradation impurities, particularly in sensitive drugs like pemetrexed dipotassium. Therefore, each stage of the freeze-drying process should be carefully tailored to achieve a stable pharmaceutically acceptable lyophilized product having long-term stability, rapid reconstitution, and regulatory compliance which are directly related to patient safety and therapeutic success.

In accordance with the invention, the inventors have been able to achieve superior control over the moisture content of the lyophilized composition by applying a unique freeze-drying process comprising annealing process. The inventor has surprisingly found a sustained control over the water content throughout the storage period of at least 12 months, at least 24 months or at least 36 months typically less than 2% w/w. Coupled through a combination of a unique freeze drying process and using only hydrochloric acid as a single pH modifying agent to achieve the desired pH, surprisingly low levels of impurities were generated in the lyophilized composition comprising pemetrexed dipotassium even after storage of at least 12, at least 24 months or at least 36 months in a sealed and sterile vial at a temperature of 25° C.

In further embodiments, the present invention provides the process of freeze-drying for the manufacturing of the lyophilized composition comprising pemetrexed dipotassium, mannitol and hydrochloric acid as a pH modifier, wherein the process of freeze-drying comprises, (a) cooling, (b) annealing, (c) primary drying, and (d) secondary drying.

In some embodiments, the present invention is directed to reconstitutable lyophilized pharmaceutical composition, comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein the composition is prepared by a process comprising:

(a) dissolving mannitol in water for injection at about 13±3° C. to obtain a clear solution;

(b) adding a portion of the mannitol solution to a container containing pemetrexed dipotassium as pemetrexed dipotassium heptahydrate on anhydrous basis to obtain a slurry;

(c) adding the slurry to the bulk of the mannitol solution and stirring until a clear solution is obtained;

(d) adjusting the pH of the clear solution with hydrochloric acid from about 6.6 to about 7.8;

(e) adjusting the volume of the solution by adding the water for injection to obtain a bulk solution with target drug concentration;

(f) sterilizing the bulk solution using a pre-sterilized 0.22 μm filter;

(g) aseptically transferring the sterile bulk solution to a vial and partially stoppering the vial under nitrogen wherein the bulk solution filed in vial is cooled to about 8° C. for freeze drying, wherein the freeze-drying process comprises;

(1) freezing the bulk solution in a vial in accordance with the following steps sequentially to perform annealing;

(A) exposing the bulk solution obtained from step (g) to a temperature ranging from about −30° C. to about −50° C. and holding it for from about 70 to about 90 minutes;

(B) exposing the product of step (A) to temperature ranging from about −5° C. to about −15° C. and holding it for from about 50 to about 70 minutes;

(C) exposing the product of step (B) to temperature ranging from about −30° C. to about −50° C. and holding it for from about 95 to about 125 minutes;

(2) performing a primary drying of the product obtained of step (1) (C) at a temperature of from about −17° C. to about 25° C.; and (3) performing a secondary drying of product obtained in the step (2) at about 45° C.

(h) completely stoppering the vials after completion of freeze-drying process under filtered nitrogen; and (i) sealing and packing the vial;

wherein after storage for at least 12 months at a temperature of 25° C., the composition in the vial comprises:

(a) not more than 0.6% w/w total impurities;

(b) not more than 2% w/w total water content; and (c) not more than 0.6% w/w total degradation impurities; wherein the degradation impurities are selected from:

(i) impurity-B in an amount that does not exceed 0.1% w/w;

(ii) impurity-C in an amount that does not exceed 0.1% w/w;

(iii) impurity-E in an amount that does not exceed 0.1% w/w;

(iv) ketopemetrexed in an amount that does not exceed 0.2% w/w; and a combination of two or more thereof.

In some embodiments, the present invention is directed to reconstitutable lyophilized pharmaceutical composition, comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein the composition is prepared by a process comprising:

(a) dissolving mannitol in water for injection at about 13±3° C. to obtain a clear solution;

(b) adding a portion of the mannitol solution to a container containing pemetrexed dipotassium as pemetrexed dipotassium heptahydrate on anhydrous basis to obtain a slurry;

(c) adding the slurry to the bulk of the mannitol solution and stirring until a clear solution is obtained;

(d) adjusting the pH of the clear solution with hydrochloric acid from about 6.6 to about 7.8;

(e) adjusting the volume of the solution by adding the water for injection to obtain a bulk solution with target drug concentration;

(f) sterilizing the bulk solution using a pre-sterilized 0.22 μm filter;

(g) aseptically transferring the sterile bulk solution to a vial and partially stoppering the vial under nitrogen wherein the bulk solution filed in vial is cooled to about 8° C. for freeze drying, wherein the freeze-drying process comprises;

(1) freezing the bulk solution in a vial in accordance with the following steps sequentially to perform annealing;

(A) exposing the bulk solution obtained from step (g) to a temperature ranging from about −30° C. to about −50° C. and holding it for from about 70 to about 90 minutes;

(B) exposing the product of step (A) to temperature ranging from about −5° C. to about −15° C. and holding it for from about 50 to about 70 minutes;

(C) exposing the product of step (B) to temperature ranging from about −30° C. to about −50° C. and holding it for from about 95 to about 125 minutes;

(2) performing a primary drying of the product obtained of step (1) (C) at a temperature of from about −17° C. to about 25° C.; and (3) performing a secondary drying of product obtained in the step (2) at about 45° C.

(h) completely stoppering the vials after completion of freeze-drying process under filtered nitrogen; and (i) sealing and packing the vial;

wherein after storage for at least 12 months at a temperature of 25° C., the composition in the vial comprises:

(a) not more than 0.6% w/w total impurities;

(b) not more than 2% w/w total water content; and (c) not more than 0.6% w/w total degradation impurities; wherein the degradation impurities are selected from:

(i) impurity-B in an amount that does not exceed 0.05% w/w;

(ii) impurity-C in an amount that does not exceed 0.05% w/w;

(iii) impurity-E in ana amount that does not exceed 0.04% w/w;

(iv) ketopemetrexed in an amount that does not exceed 0.15% w/w, and a combination of two or more thereof.

In some embodiments, the present invention is directed to reconstitutable lyophilized pharmaceutical composition, comprising pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg;

a pH modifying component consisting essentially of hydrochloric acid; with the proviso that the pH modifying component does not include a hydroxide base, wherein the composition is prepared by a process comprising:

(a) dissolving mannitol in water for injection at about 13±3° C. to obtain a clear solution;

(b) adding a portion of the mannitol solution to a container containing pemetrexed dipotassium as pemetrexed dipotassium heptahydrate on anhydrous basis to obtain a slurry;
(c) adding the slurry to the bulk of the mannitol solution and stirring until a clear solution is obtained;
(d) adjusting the pH of the clear solution with hydrochloric acid from about 6.6 to about 7.8;
(e) adjusting the volume of the solution by adding the water for injection to obtain a bulk solution with target drug concentration;
(f) sterilizing the bulk solution using a pre-sterilized 0.22 μm filter;
(g) aseptically transferring the sterile bulk solution to a vial and partially stoppering the vial under nitrogen wherein the bulk solution filed in vial is cooled to about 8° C. for freeze drying, wherein the freeze-drying process comprises;
(1) freezing the bulk solution in a vial in accordance with the following steps sequentially to perform annealing;
(A) exposing the bulk solution obtained from step (g) to a temperature ranging from about −30° C. to about −50° C. and holding it for from about 70 to about 90 minutes;
(B) exposing the product of step (A) to temperature ranging from about −5° C. to about −15° C. and holding it for from about 50 to about 70 minutes;
(C) exposing the product of step (B) to temperature ranging from about −30° C. to about −50° C. and holding it for from about 95 to about 125 minutes;
(2) performing a primary drying of the product obtained of step (1) (C) at a temperature of from about −17° C. to about 25° C.; and
(3) performing a secondary drying of product obtained in the step (2) at about 45° C.

(h) completely stoppering the vials after completion of freeze-drying process under filtered nitrogen; and
(i) sealing and packing the vial;

wherein after storage for at least 24 months at a temperature of 25° C., the composition in the vial comprises:
(a) not more than 1% w/w total impurities;
(b) not more than 2% w/w total water content; and
(c) not more than 0.6% w/w total degradation impurities; wherein the degradation impurities are selected from:
(i) impurity-B in an amount that does not exceed 0.1% w/w;
(ii) impurity-C in an amount that does not exceed 0.1% w/w;
(iii) impurity-E in an amount that does not exceed 0.1% w/w;
(iv) ketopemetrexed in an amount that does not exceed 0.2% w/w; and a combination of two or more thereof.

In some embodiments, the storage period of the lyophilized composition is at least 36 months at a temperature of 25° C.

In some embodiments, the present invention provides the process, wherein the process comprises dissolving mannitol at a concentration of up to 40 mg/ml in water for injection to obtain clear solution; and adding the slurry of pemetrexed dipotassium heptahydrate (which is made in water) to the bulk solution of mannitol and made clear solution, wherein the concentration of pemetrexed dipotassium is up to 40 mg/ml in bulk solution.

In some embodiments, the pH of the lyophilized composition is measured by reconstituting the composition with 0.9% sodium chloride injection or 5% dextrose solution for injection. In some embodiments, the lyophilized composition has a pH from 6.6 to 7.8, when measured after reconstitution with 0.9% sodium chloride injection or 5% dextrose solution for injection. In certain embodiments, the lyophilized composition has a pH from 6.8 to 7.1, when measured after reconstitution with 0.9% sodium chloride injection or 5% dextrose solution for injection.

In some embodiments, the pH of the solution is adjusted during the manufacturing process by using hydrochloric acid as a pH modifying component prior to lyophilization step. In some embodiments, the present invention provides the process to prepare composition, wherein the pH of the solution is adjusted from about 6.6 to about 7.8 by using hydrochloric acid as pH modifying component prior to lyophilization, with the proviso that the pH modifying component used to adjust the pH does not include a hydroxide base. In some embodiments, the present invention provides the process to prepare composition, wherein the pH of the solution is adjusted from about 6.9 to about 7.1 by using hydrochloric acid as pH modifying component prior to lyophilization, with the proviso that the pH modifying component used to adjust the pH does not include a hydroxide base.

Annealing is a controlled thermal treatment step performed during or after the initial freezing phase of lyophilization. During annealing, after the product is rapidly frozen, the temperature is deliberately increased to a specific point, but still below the glass transition temperature and held steady for a set period, without applying a vacuum. This pause allows molecular mobility within the frozen matrix, encouraging crystallization of certain components (such as bulking agents like mannitol) and the growth of larger ice crystals. These larger ice crystals and pores formed during annealing reduce resistance to water vapor flow during primary drying, accelerating the drying process and making it more uniform across vials. Its primary purpose is to optimize the physical structure of the frozen product, which directly impacts the efficiency and quality of subsequent drying stages. It is a tool for optimizing lyophilization cycles and improving the quality and stability of freeze-dried pharmaceuticals composition.

In some embodiments, the present invention provides the process wherein the composition having pemetrexed dipotassium in an amount of about 118.3 mg equivalent to 100 mg of pemetrexed and mannitol in an amount of about 106 mg, the annealing process comprises the following steps sequentially:
(a) freezing the composition solution at a temperature of about −36° C. and holding for about 80 minutes;
(b) bringing the temperature to about −10° C. and holding it for about 60 minutes; and
(c) freezing at a temperature of about −35° C. and holding it for a time of about 100 minutes, or wherein the composition having pemetrexed dipotassium in an amount of about 591.5 mg equivalent to 500 mg pemetrexed comprises and mannitol in an amount of about 500 mg, the annealing process comprises the following steps sequentially,
(a) freezing the composition solution at a temperature of about −45° C. and holding it for about 80 minutes;
(b) bringing the temperature to about −10° C. and holding it for about 60 minutes; and
(c) freezing at a temperature of about −45° C. and holding it for about 120 minutes.

In further embodiments, the present invention provides the process of freeze-drying for the manufacturing of the lyophilized composition comprising pemetrexed dipotassium in an amount of about 118.3 mg equivalent to 100 mg of pemetrexed, mannitol in an amount of about 106 mg and hydrochloric acid as a pH modifier, wherein the primary drying process comprises the following steps sequentially (a) freezing at a temperature of about −17° C. and holding for about 800 minutes;

(b) bringing the temperature to about −5° C. and holding it for about 480 minutes; and (c) bringing the temperature to about 25° C. and holding it for about 180 minutes.

In further embodiments, the present invention provides the process of freeze-drying for the manufacturing of the lyophilized composition comprising pemetrexed dipotassium in an amount of about 118.3 mg equivalent to 100 mg of pemetrexed, mannitol in an amount of about 106 mg and hydrochloric acid as a pH modifier, wherein the secondary drying process comprises the step of treating the vial obtained after primary drying at about 45° C. and holding it for about 550 minutes.

In further embodiments, the present invention provides the process of freeze-drying for the manufacturing of the lyophilized composition comprising pemetrexed dipotassium in an amount of about 591.5 mg equivalent to 500 mg pemetrexed, mannitol in an amount of about 500 mg and hydrochloric acid as a pH modifier, wherein the process of primary drying comprises (a) freezing at a temperature of about −17° C. and holding it for about 640 minutes;

(b) bringing the temperature to about −5° C. and holding it for about 1020 minutes;

(c) bringing the temperature to about 6° C. and holding it for about 60 minutes;

(d) bringing the temperature to about 15° C. and holding it for about 60 minutes; and (e) bringing the temperature to about 23° C. and holding it for about 60 minutes.

In further embodiments, the present invention provides the process of freeze-drying for the manufacturing of the lyophilized composition comprising pemetrexed dipotassium in an amount of about 591.5 mg equivalent to 500 mg pemetrexed, mannitol in an amount of about 500 mg and hydrochloric acid as a pH modifier, wherein the secondary drying process comprises the step of treating the vial obtained after primary drying at about 45° C. and holding it for about 1150 minutes.

The lyophilized pharmaceutical composition of the present invention comprises the active pharmaceutical ingredient in the form of a potassium rather than a sodium salt has an additional advantage to a patient particularly for patients suffering from or at risk of cardiovascular disorders, including but not limited to hypertension, congestive heart failure, and edema. The use of non-sodium salts minimizes the sodium burden associated with chronic drug administration and thereby reduces the risk of sodium-induced fluid retention, elevated blood pressure, and cardiovascular stress.

In some embodiments, the pharmaceutical composition comprises pemetrexed in the form of a dipotassium salt, rather than its disodium counterpart, thereby providing a substantially low sodium ion to cardiovascular patients.

In some embodiments, the present provides a method of treating non-squamous NSCLC or mesothelioma to a patient in need thereof comprises administration a reconstitutable lyophilized pharmaceutical composition comprises pemetrexed dipotassium, mannitol in an amount and a pH modifying component consisting essentially of hydrochloric acid; with the proviso that the pH modifying component does not include a hydroxide base, wherein the composition having pemetrexed dipotassium is free of sodium ions released during the dilution of pemetrexed disodium, to avoid or reduce the administration of sodium ions to the patient.

In some embodiments, the present provides a method of treating non-squamous NSCLC or mesothelioma to a patient in need thereof comprises administration of a reconstitutable lyophilized pharmaceutical composition comprises pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base.

In some embodiments, the present provides a method of treating non-squamous NSCLC or mesothelioma to a patient in need thereof comprises administration of a reconstitutable lyophilized pharmaceutical composition comprises pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein the lyophilized composition has a pH from 6.6 to 7.8, when measured after reconstitution with 0.9% sodium chloride injection or 5% dextrose solution for injection.

In some embodiments, the present provides a method of treating non-squamous NSCLC or mesothelioma to a patient in need thereof, comprising administering a reconstitutable lyophilized pharmaceutical composition comprises pemetrexed dipotassium selected in an amount of about 118.3 mg equivalent to 100 mg of pemetrexed and mannitol in an amount of about 106 mg; or pemetrexed dipotassium in an amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide base, wherein after at least 12 months at a temperature of 25° C., the composition comprises:

(a) not more than 0.6% w/w total impurities;

(b) not more than 2% w/w total water content; and (c) not more than 0.6% w/w total degradation impurities; wherein the degradation impurities are selected from:

(i) impurity-B in an amount that does not exceed 0.1% w/w;

(ii) impurity-C in an amount that does not exceed 0.1% w/w;

(iii) impurity-E in an amount that does not exceed 0.1% w/w;

(iv) ketopemetrexed in an amount that does not exceed 0.2% w/w; and a combination of two or more thereof.

In some embodiments, the present provides a method of treating non-squamous NSCLC or mesothelioma to a patient in need thereof, comprising administering a reconstitutable lyophilized pharmaceutical composition comprises pemetrexed dipotassium selected in an amount of about 118.3 mg equivalent to 100 mg of pemetrexed and mannitol in an amount of about 106 mg; or pemetrexed dipotassium in an amount of about amount of about 591.5 mg equivalent to 500 mg pemetrexed and mannitol in an amount of about 500 mg; and a pH modifying component consisting essentially of hydrochloric acid; with the proviso that the pH modifying component does not include a hydroxide, wherein after at least 24 months at a temperature of 25° C., the composition comprises:

(a) not more than 1% w/w total impurities;
(b) not more than 2% w/w total water content; and
(c) not more than 0.6% w/w total degradation impurities; wherein the degradation impurities are selected from:
  (i) impurity-B in an amount that does not exceed 0.1% w/w;
  (ii) impurity-C in an amount that does not exceed 0.1% w/w;
  (iii) impurity-E in an amount that does not exceed 0.1% w/w;
  (iv) ketopemetrexed in an amount that does not exceed 0.2% w/w; and a combination of two or more thereof.

In one of the above embodiments, the storage period of the lyophilized composition is selected as at least 36 months at a temperature of 25° C.

In some embodiments, the present invention provides a method of treating non-squamous NSCLC or mesothelioma to a patient in need thereof comprises administration of a reconstitutable lyophilized pharmaceutical composition, wherein the lyophilized composition has a pH from 6.6 to 7.8, when measured after reconstitution with 0.9% sodium chloride injection or 5% dextrose solution for injection. In certain embodiments, the present provides a method of treating non-squamous NSCLC or mesothelioma to a patient in need thereof comprises administration of a reconstitutable lyophilized pharmaceutical composition, wherein the lyophilized composition has a pH from 6.8 to 7.1, when measured after reconstitution with 0.9% sodium chloride injection or 5% dextrose solution for injection.

In some embodiments, the present invention provides a method of treating non-squamous NSCLC or mesothelioma to a patient in need thereof comprises administration of a reconstitutable lyophilized pharmaceutical composition, wherein the lyophilized composition is reconstituted with 0.9% sodium chloride solution for injection or 5% dextrose solution for injection.

In some embodiments, the present invention provides a method of treating non-squamous NSCLC or mesothelioma to a patient in need thereof comprises administration of a reconstitutable lyophilized pharmaceutical composition, wherein the concentration of pemetrexed achieved after reconstitution with 0.9% sodium chloride solution for injection or 5% dextrose solution for injection is 25 mg/mL. In some embodiments, following reconstitution, the solution is further diluted to a final pemetrexed concentration of 1 mg/mL to 5 mg/mL for intravenous infusion to a patient in need thereof. In further embodiments, the infusion media used to administer the patient is selected from with 0.9% sodium chloride solution for injection or 5% dextrose solution for injection In some embodiments, the present provides a method of treating non-squamous NSCLC or mesothelioma to a patient in need thereof comprises administration of a reconstitutable lyophilized pharmaceutical composition, wherein the reconstitution time of the composition with 0.9% sodium chloride solution for injection or 5% dextrose solution for injection is less than 70 seconds.

In some embodiments, the present provides a method of treating non-squamous NSCLC or mesothelioma to a patient in need thereof comprises administration of a reconstitutable lyophilized pharmaceutical composition, wherein the reconstituted solution is free from particulate matter and stable at 2-8° C. for 24 hours from the time of reconstitution. In some embodiments, stable at 2-8° C. for 24 hours from the time of reconstitution refers to reconstitution stability, wherein the composition remains stable enough for administration to patient in need thereof with maintaining physical, and chemical stability as per regulatory norms.

Any embodiments specifically and explicitly recited herein may form the basis of a disclaimer either alone or in combination with one or more further embodiments. Hereinafter, the invention will be more specifically described by way of Examples. The examples are not intended to limit the scope of the invention and are merely used as illustrations.

EXAMPLES

Example 1: Pemetrexed Dipotassium Composition Equivalent to Pemetrexed 100 mg/Vial

TABLE 2

| S.No. | Ingredients | Function | Quantity/ml | 100 mg/ vial |
|---|---|---|---|---|
| 1 | Pemetrexed Dipotassium (on anhydrous basis) equivalent to Pemetrexed as pemetrexed dipotassium heptahydrate | Active pharmaceutical ingredient | 29.575 mg of Pemetrexed dipotassium (25.000 mg of Pemetrexed) | 118.300 mg (~100.00 mg Pemetrexed) |
| 2 | Mannitol | Bulking agent | 26.50 mg | 106.000 mg |
| 3 | Hydrochloric acid | Acidifying agent | Q.s for pH adjustment | Q.s for pH adjustment |
| 4 | Water for injection | Solvent | q.s to 1.0 mL | Q.s to 4.00 mL |
| 5 | Nitrogen | During compounding and to transfer the product through filtration train during filtration, filling and post flushing of lyophilized product. | As required | As required |

*QS = quantity sufficient (a) Under constant stirring, the dispensed quantity of mannitol was added to water for injection at a temperature of 13±3° C. in a compounding vessel and mixed for at least 10 minutes or until a clear solution was formed.

(b) A required quantity of this mannitol solution from step (a) was transferred to a container containing the weighed pemetrexed dipotassium as pemetrexed dipotassium heptahydrate on anhydrous basis and shaken to form a uniform and easily transferable slurry;

(c) The slurry from step (b) was added to the compounding vessel having the bulk solution of mannitol and stirred at 300±25 rpm for at least 10 minutes, or until visually dissolved;

(d) the pH of the clear solution was adjusted with 0.1N hydrochloric acid to 7.0±0.1;

(e) volume of the solution was adjusted by adding the water for injection to obtain a bulk solution with target drug concentration;

(f) the bulk solution was sterilized by passage through pre-sterilized 0.22 μm filter;

(g) the sterile bulk solution was transferred aseptically to vial and partially stoppered the vial under nitrogen for freeze drying wherein the freeze-drying process includes:

| Stage | Temperature | Ramp | Hold | Vacuum (mbar) |
|---|---|---|---|---|
| Loading | 8 | NA | NA | NA |
| Freezing | −36 | 200 | 80 | NA |
| with | −10 | 60 | 60 | NA |
| annealing | −35 | 60 | 100 | NA |
| Primary | −17 | 120 | 800 | 263 |
| drying | −5 | 80 | 480 | 263 |
| | 25 | 150 | 180 | 263 |
| Secondary drying | 45 | 30 | 550 | 38 |

(h) the vials were stoppered completely after completion of freeze drying under filtered nitrogen, which are finally sealed and packed.

The results of the physical and chemical parameters of PAMBE1035 (equivalent to pemetrexed 100 mg/vial) obtained initially after manufacturing are described below in Table 3.

TABLE 3

| S. No | Parameter | Type of impurities | Initial |
|---|---|---|---|
| 1 | Assay by HPLC * | — | 102.4% |
| 2 | Water content by KF | — | 1.0% w/w |
| 3 | Reconstitution time | — | 50 Seconds |
| 4 | pH | — | 7.0 |
| 5 | Related substance by HPLC (% w/w) | | |
| | (i) Impurity-B | Degradant | <0.04% |
| | (ii) Impurity-C | Degradant | <0.04% |
| | (iii) Impurity-E | Degradant | <0.04% |
| | (iv) Ketopemetrexed | Degradant | 0.05% |
| | (v) total degradation impurities | — | <0.6% |
| | (vi) single specified impurity | — | <0.1% |
| | (vii) single unspecified impurity | — | <0.2% |
| | (viii) Total impurities | — | 0.08% |
| | (ix) Impurity-G** | chiral impurity | <0.05% |

* Labeled amount: Each vial contains Pemetrexed dipotassium equivalent to Pemetrexed 100 mg/vial

**Impurity G was tested using chiral chromatography using chiral column at a wavelength of about 230 nm, using mixture of hexane, isopropanol, ethanol and trifluoroacetic acid in a suitable proportion. The impurity was measured and reported as % w/w.

***Impurities B, Impurities C, Impurities E, ketopemetrexed or any single specified or unspecified impurities were tested using gradient reverse phase chromatography using C-18 column at a wavelength of about 250 nm using mixture of ammonium formate buffer of about pH 3.5 and acetonitrile in a suitable proportion. The impurities were measured and reported as % w/w.

Conclusion: The initial analytical results of prepared composition of pemetrexed for Injection (as dipotassium) 100 mg/vial was found satisfactory across all physical and chemical parameters.

Example 2: Pemetrexed Dipotassium Composition Equivalent to Pemetrexed 500 mg/Vial

TABLE 4

| S.No. | Ingredients | Function | Quantity/mL | Quantity/ Unit |
|---|---|---|---|---|
| 1 | Pemetrexed Dipotassium (on anhydrous basis) equivalent to Pemetrexed as pemetrexed dipotassium heptahydrate | Active pharmaceutical ingredient | 29.575 mg (25.000 mg of Pemetrexed) | 591.500 mg (~500 mg Pemetrexed) |
| 2 | Mannitol | Bulking agent | 25.00 mg | 500.000 mg |
| 3 | Hydrochloric acid | Acidifying agent | QS for pH adjustment | QS for pH adjustment |
| 4 | Water for injection | Solvent | QS to 1.0 mL | QS to 20.00 mL |
| 5 | Nitrogen | During compounding and to transfer the product through filtration train during filtration, filling and post flushing of lyophilized product. | As required | As required |

*QS = quantity sufficient (a) Under constant stirring, the dispensed quantity of mannitol was added to water for injection at a temperature of 13±3° C. in a compounding vessel and mixed for at least 10 minutes or until a clear solution was formed.

(b) A required quantity of this mannitol solution from step (a) was transferred to a container containing the weighed pemetrexed dipotassium as pemetrexed dipotassium heptahydrate on anhydrous basis and shaken to form a uniform and easily transferable slurry;

(c) The slurry from step (b) was added to the compounding vessel having the bulk solution of mannitol and stirred at 300±25 rpm for at least 10 minutes, or until visually dissolved;

(d) the pH of the clear solution was adjusted with 0.1N hydrochloric acid to 7.0±0.1;

(e) volume of the solution was adjusted by adding the water for injection to obtain a bulk solution with target drug concentration;

(f) the bulk solution was sterilized by passage through pre-sterilized 0.22 μm filter;

(g) the sterile bulk solution was transferred aseptically to vial and partially stoppered the vial under nitrogen for freeze drying wherein the freeze-drying process includes:

| Stage | Temperature | Ramp | Hold | Vacuum (mbar) |
|---|---|---|---|---|
| Loading | 8 | — | — | — |
| Freezing | −45 | 200 | 80 | NA |
| with | −10 | 60 | 60 | NA |
| annealing | −45 | 60 | 120 | NA |
| Primary | −17 | 120 | 640 | 188 |
| drying | −5 | 50 | 1020 | 150 |
| | 6 | 20 | 60 | 113 |
| | 15 | 20 | 60 | 113 |
| | 23 | 30 | 60 | 113 |
| Secondary drying | 45 | 20 | 1150 | 38 |

(h) the vials were stoppered completely after completion of freeze drying under filtered nitrogen, which are finally sealed and packed.

The results of the physical and chemical parameters of PAMAE1015 (equivalent to pemetrexed 500 mg/vial) obtained initially after manufacturing are described in Table 5 (below).

TABLE 5

| S. No | Parameter | Type of impurities | Initial |
|---|---|---|---|
| 1 | Assay by HPLC * | — | 102.4% |
| 2 | Water content by KF | — | 0.9% w/w |
| 3 | Reconstitution time | — | 56 seconds |
| 4 | pH | — | 6.9 |
| 5 | Related substance by HPLC (% w/w) | | |
| | (i) Impurity-B | Degradant | <0.04% |
| | (ii) Impurity-C | Degradant | <0.04% |
| | (iii) Impurity-E | Degradant | <0.04% |
| | (iv) Ketopemetrexed | Degradant | 0.08% |
| | (v) Total degradation impurities | — | <0.6% |
| | (vi) Single specified impurity | — | <0.1% |
| | (vii) Single unspecified impurity | — | <0.2% |

TABLE 5-continued

| S. No | Parameter | Type of impurities | Initial |
|---|---|---|---|
| | (vii) Total impurities | — | 0.11% |
| | (ix) Impurity-G** | chiral impurity | <0.05% |

* Labeled amount: Each vial contains Pemetrexed dipotassium equivalent to Pemetrexed 500 mg/vial

**Impurity G was tested using chiral chromatography using chiral column at a wavelength of about 230 nm, using mixture of hexane, isopropanol, ethanol and trifluoroacetic acid in a suitable proportion. The impurity was measured and reported as % w/w.

***Impurities B, Impurities C, Impurities E, ketopemetrexed or any single specified or unspecified impurities were tested using gradient reverse phase chromatography using C-18 column at a wavelength of about 250 nm using mixture of ammonium formate buffer of about pH 3.5 and acetonitrile in a suitable proportion. The impurities were measured and reported as % w/w.

Conclusion: The initial analytical results of prepared composition of pemetrexed for Injection (as dipotassium) 500 mg/vial was found satisfactory across all physical and chemical parameters.

Example 3: Reconstitution Solution Stability Study of Pemetrexed for Injection 100 mg/Vial Reconstitution solution stability study of Pemetrexed for Injection 100 mg/vial (Batch #PEMBE1035) prepared according to Example 1 was executed using 5% dextrose solution for injection as the primary diluent and obtained a final concentration of pemetrexed as 25 mg/mL for 100 mg per vial strength. The in-use stability of the reconstituted product was also evaluated in accordance with the storage recommendations after reconstitution, at 2° C. to 8° C. up to 24 hours. Table 6 (below) describes the results of reconstitution stability of pemetrexed for injection 100 mg/vial. The results of reconstitution solution stability of Batch #PEMBE1035, Pemetrexed for Injection 100 mg/vial [5% Dextrose solution for Injection, USP] which is approximately 25 mg/mL as Pemetrexed are described in Table 6 (below).

TABLE 6

| S. No | Parameter | Type of impurities | Initial (Room Temperature) | 24 hours (2° C.-8° C.) |
|---|---|---|---|---|
| 1 | Assay by HPLC * | — | 95.6 | 94.7 |
| 2 | Description | — | White lyophilized cake | White lyophilized cake |
| 3 | Description (After reconstitution) | — | Clear colorless solution | Clear colorless solution |
| 4 | Reconstitution Time | — | <70 sec | NA |
| 5 | Osmolality (mOsm) | — | 532<br>529<br>533 | 535<br>537<br>534 |
| 6 | Particulate matter | — | 10 μm: 502<br>25 μm: 4 | 10 μm: 380<br>25 μm: 10 |
| 7 | Related substance by HPLC (% w/w) | | | |
| | (i) Impurity-B | Degradant | <0.04% | <0.04% |
| | (ii) Impurity-C | Degradant | <0.04% | <0.04% |
| | (iii) Impurity-E | Degradant | <0.04% | <0.04% |
| | (iv) Ketopemetrexed | Degradant | <0.2% | <0.2% |
| | (v) Total degradation impurities | — | <0.6% | <0.6% |
| | (vi) Single specified impurity | — | <0.1% | <0.1% |
| | (viii) Single unspecified impurity | — | <0.2% | <0.2% |
| | (vi) Total impurities | — | <1% | <1% |

TABLE 6-continued

| S. No | Parameter | Type of impurities | Initial (Room Temperature) | 24 hours (2° C.-8° C.) |
|---|---|---|---|---|
| | (vii) Impurity-G** | chiral impurity | <0.05% | <0.05% |

* Labelled amount: Each vial contains Pemetrexed dipotassium equivalent to Pemetrexed 100 mg/vial
**Impurity G was tested using chiral chromatography using chiral column at a wavelength of about 230 nm, using mixture of hexane, isopropanol, ethanol and trifluoroacetic acid in a suitable proportion. The impurity was measured and reported as % w/w.
***Impurities B, Impurities C, Impurities E, ketopemetrexed or any single specified or unspecified impurities were tested using gradient reverse phase chromatography using C-18 column at a wavelength of about 250 nm using mixture of ammonium formate buffer of about pH 3.5 and acetonitrile in a suitable proportion. The impurities were measured and reported as % w/w.

Conclusion: The analytical results of reconstituted solution stability study of pemetrexed for Injection (as dipotassium) 100 mg/vial with 5% Dextrose solution for Injection, USP (concentration of 25 mg/mL) was found satisfactory across all physical and chemical, when stored at 2° C. to 8° C. for 24 hours.

Example 4: Reconstitution Solution Stability Study of Pemetrexed for Injection 500 mg/Vial Reconstitution solution stability study of Pemetrexed for Injection 500 mg/vial (Batch #PEMAE1015) prepared according to example 2 was executed using 5% dextrose solution for injection as the primary diluent and obtained a final concentration of pemetrexed as 25 mg/mL for 500 mg per vial strength. The in-use stability of the reconstituted product was also evaluated in accordance with the storage recommendations after reconstitution, at 2° C. to 8° C. up to 24 hours. Table 7 (below) describes the results of reconstitution stability of pemetrexed for injection 500 mg/vial.

The results of reconstitution solution stability of Batch #PEMBE1015, Pemetrexed for Injection 500 mg/vial [5% Dextrose solution for Injection, USP] which is approximately 25 mg/mL as Pemetrexed are described below in Table 7.

TABLE 7

| S. No | Parameter | Type of impurities | Initial (Room Temperature) | 24 hours (2° C.-8° C.) |
|---|---|---|---|---|
| 1 | Assay by HPLC * | — | 97.0 | 98.8 |
| 2 | Description | — | White lyophilized cake | White lyophilized cake |
| 3 | Description (After reconstitution) | — | Clear colourless solution | Clear colourless solution |
| 4 | Reconstitution Time | — | <70 sec | NA |
| 5 | Osmolality (mOsm) | — | 538<br>539<br>537 | 541<br>543<br>547 |
| 6 | Particulate matter | — | 10 μm: 132<br>25 μm: 6 | 10 μm: 132<br>25 μm: 6 |
| 7 | Related substance by HPLC (% w/w) | | | |
| | (i) Impurity-B | Degradant | <0.04% | <0.04% |
| | (ii) Impurity-C | Degradant | <0.04% | <0.04% |
| | (iii) Impurity-E | Degradant | <0.04% | <0.04% |
| | (iv) Ketopemetrexed | Degradant | <0.2% | <0.2% |
| | (v) Total degradation impurities | — | <0.6% | <0.6% |
| | (vi) Single specified impurity | — | <0.1% | <0.1% |
| | (vii) Single unspecified impurity | — | <0.02% | <0.02% |
| | (vi) Total impurities | — | <1% | <1% |
| | (vii) Impurity-G** | chiral impurity | <0.05% | <0.05% |

* Labeled amount: Each vial contains Pemetrexed dipotassium equivalent to Pemetrexed 100 mg/vial
**Impurity G was tested using chiral chromatography using chiral column at a wavelength of about 230 nm, using mixture of hexane, isopropanol, ethanol and trifluoroacetic acid in a suitable proportion. The impurity was measured and reported as % w/w.
***Impurities B, Impurities C, Impurities E, ketopemetrexed or any single specified or unspecified impurities were tested using gradient reverse phase chromatography using C-18 column at a wavelength of about 250 nm using mixture of ammonium formate buffer of about pH 3.5 and acetonitrile in a suitable proportion. The impurities were measured and reported as % w/w.

Conclusion: The analytical results of reconstituted solution stability study of Pemetrexed for Injection (as dipotassium) 500 mg/vial with 5% Dextrose solution for Injection, USP (concentration of 25 mg/mL) was found satisfactory across all physical and chemical parameters, when stored at 2° C. to 8° C. for 24 hours.

Example 5: Long Term Stability Testing of Pemetrexed for Injection 100 mg/Vial at 25° C. And 60% Relative Humidity Stability testing: The lyophilized vials, which were manufactured according to Example 1 (filled, sealed, lyophilized vials) were subjected to storage stability testing at 25° C., 60% relative humidity for 12 months, 24 months and 36 months. The assay of drug as well as content of known and unknown impurities was analyzed initially and after given storage time and condition. The content of total impurities and individual impurities were analyzed by HPLC or high-performance liquid chromatography method. The results are summarized in Table 8 (below).

TABLE 8

Long term Stability Study data for pemetrexed for injection 100 mg/Vial, when stored at 25° C., 60% relative humidity (Batch: PEMBE1035)

| S. No | Parameter | Type of impurities | Initial | After 12 Months | After 24 Months | After 36 Months |
|---|---|---|---|---|---|---|
| 1 | Assay by HPLC * | — | 102.4% | 102.7% | 100.6% | 102.4% |
| 2 | Water content by KF | — | 1.0% w/w | 1.3% w/w | 1.6% w/w | 1.8% w/w |
| 3 | Reconstitution time | — | 50 Seconds | 54 Seconds | 53 Seconds | 67 Seconds |
| 4 | pH | — | 7.0 | 6.8 | 7.0 | 6.8 |
| 5 | Related substance by HPLC ( % w/w) | | | | | |
| | (i) Impurity-B | Degradant | <0.04% | <0.04% | <0.04% | <0.04% |
| | (ii) Impurity-C | Degradant | <0.04% | <0.04% | <0.04% | <0.04% |
| | (iii) Impurity-E | Degradant | <0.04% | <0.04% | <0.04% | <0.04% |
| | (iv) Ketopemetrexed | Degradant | 0.05% | 0.08% | 0.11% | 0.11% |

TABLE 8-continued

Long term Stability Study data for pemetrexed for injection 100 mg/Vial, when stored at 25° C., 60% relative humidity (Batch: PEMBE1035)

| S. No | Parameter | Type of impurities | Initial | After 12 Months | After 24 Months | After 36 Months |
|---|---|---|---|---|---|---|
| | (v) Total degradation impurities | — | <0.6% | <0.6% | <0.6% | <0.6% |
| | (vi) Single specified impurity | — | <0.1% | <0.1% | <0.1% | <0.1% |
| | (vii) Single unspecified impurity | — | <0.2% | <0.2% | <0.2% | NMT 0.2%** |
| | (viii) Total impurities | — | 0.08% | 0.17% | 0.47% | 0.65% |
| | (ix) Impurity-G*** | chiral impurity | <0.05% | <0.05% | <0.05% | <0.05% |

* Labeled amount: Each vial contains Pemetrexed dipotassium equivalent to Pemetrexed 100 mg/vial

**NMT= not more than

***Impurity G was tested using chiral chromatography using chiral column at a wavelength of about 230 nm, using mixture of hexane, isopropanol, ethanol and trifluoroacetic acid in a suitable proportion. The impurity was measured and reported as % w/w.

**** Impurities B, Impurities C, Impurities E, ketopemetrexed or any single specified or unspecified impurities were tested using gradient reverse phase chromatography using C-18 column at a wavelength of about 250 nm using mixture of ammonium formate buffer of about pH 3.5 and acetonitrile in a suitable proportion. The impurities were measured and reported as % w/w.

Conclusion: The analytical results of long-term stability study of Pemetrexed for injection (As dipotassium) 100 mg/Vial packed in a sterile and sealed vial was found to be satisfactory across all physical and chemical parameters as evident above, when stored at 25° C. and 60% relative humidity over a period of 12 months. Further the current composition was also found to be stable after 24 months and after 36 months, indicating that the current composition was stable for extended periods beyond 12 months.

Example 6: Long Term Stability Testing of Pemetrexed for Injection 500 mg/Vial at 25° C. And 60% Relative Humidity Stability testing: The lyophilized vials, which were manufactured according to Example 2 (filled, sealed, lyophilized vials) were subjected to storage stability testing at 25° C., 60% relative humidity for 12 months, 24 months and 36 months. The assay of drug as well as content of related substances was analyzed initially and after given storage time and condition. The content of total impurities and individual impurities were analyzed by HPLC or high-performance liquid chromatography method. The results are summarized below in Table 9.

TABLE 9

Long term Stability Study data for pemetrexed for injection 500 mg/Vial, Batch No. PEMAE1015 stored at 25° C., 60% relative humidity.

| S. No | Parameter | Type of impurities | Initial | After 12 Months | After 24 Months | After 36 Months |
|---|---|---|---|---|---|---|
| 1 | Assay by HPLC * | — | 102.4% | 101.1% | 101.5% | 102.2% |
| 2 | Water content by KF | — | 0.9% w/w | 0.6% w/w | 0.8% w/w | 0.8% w/w |
| 3 | Reconstitution time | — | 56 seconds | 58 seconds | 59 seconds | 64 Seconds |
| 4 | pH | — | 6.9 | 7.0 | 6.9 | 6.9 |
| 5 | Related substance by HPLC (% w/w) | | | | | |
| | (i) Impurity-B | Degradant | <0.04% | <0.04% | <0.04% | <0.04% |
| | (ii) Impurity-C | Degradant | <0.04% | <0.04% | <0.04% | <0.04% |
| | (iii) Impurity-E | Degradant | <0.04% | <0.04% | <0.04% | <0.04% |
| | (iv) Ketopemetrexed | Degradant | 0.08% | 0.06% | 0.06% | 0.06% |
| | (v) Total degradation impurities | — | <0.6% | <0.6% | <0.6% | <0.6% |
| | (vi) Single specified impurity | — | <0.1% | <0.1% | <0.1% | <0.1% |
| | (vii) Single unspecified impurity | — | <0.2% | <0.2% | <0.2% | NMT 0.2% |
| | (viii) Total impurities | — | 0.11% | 0.10% | 0.19% | 0.19% |

TABLE 9-continued

Long term Stability Study data for pemetrexed for injection 500 mg/Vial, Batch No. PEMAE1015 stored at 25° C., 60% relative humidity.

| S. No | Parameter | Type of impurities | Initial | After 12 Months | After 24 Months | After 36 Months |
|---|---|---|---|---|---|---|
| | (ix) Impurity-G ** | chiral impurity | <0.05% | <0.05% | <0.05% | <0.05% |

* Labeled amount: Each vial contains Pemetrexed dipotassium equivalent to Pemetrexed 100 mg/vial

** NMT= not more than

** Impurity G was tested using chiral chromatography using chiral column at a wavelength of about 230 nm, using mixture of hexane, isopropanol, ethanol and trifluoroacetic acid in a suitable proportion. The impurity was measured and reported as % w/w.

*** Impurities B, Impurities C, Impurities E, ketopemetrexed or any single specified or unspecified impurities were tested using gradient reverse phase chromatography using C-18 column at a wavelength of about 250 nm using mixture of ammonium formate buffer of about pH 3.5 and acetonitrile in a suitable proportion. The impurities were measured and reported as % w/w.

Conclusion: The analytical results of long-term stability study of Pemetrexed for injection (As dipotassium) 500 mg/Vial packed in a sterile and sealed vial was found to be satisfactory across all physical and chemical parameters as evident above, when stored at 25° C. and 60% relative humidity over a period of 12 months. Further the current composition was also found to be stable after 24 months and after 36 months indicating that the current composition was stable for extended periods beyond 12 months.

Example 7: Physiological Solution Compatibility of Pemetrexed for Injection 100 mg/Vial Physiological solution compatible study of Pemetrexed for Injection 100 mg/vial (Batch #PEMBE1035) prepared according to example 1 was executed using 0.9% sodium chloride solution for injection, USP and 5% dextrose solution for injection at a final concentration of pemetrexed as 1 mg/mL. The in-use stability of the final solution product was evaluated in accordance with the storage recommendations after reconstitution, at 2° C. to 8° C. up to 24 hours. Tables 10 and 11 (below) describe the results of physiological compatibility of pemetrexed for injection 100 mg/vial.

TABLE 10

Physiological compatible study of Pemetrexed for Injection 100 mg/vial at a final concentration of 1 mg/mL with 0.9% sodium chloride solution for injection, USP

| S. No | Parameter | Type of impurities | Initial (Room Temperature) | 24 hours (2° C.-8° C.) |
|---|---|---|---|---|
| 1 | Assay by HPLC * | — | 97.3 | 97.5 |
| 2 | Description (After reconstitution) | — | Clear colorless solution | Clear colorless solution |
| 3 | pH | — | 6.84 | 6.82 |
| 4 | Particulate matter | | | |
| | Foreign matter | — | Free from foreign matter | Free from foreign matter |
| | | — | 10 μm: 236<br>25 μm: 16 | 10 μm: 144<br>25 μm: 6 |
| 5 | Related substance by HPLC (% w/w) | | | |
| | (i) Impurity-B | Degradant | 0.046 | 0.045 |
| | (ii) Impurity-C | Degradant | <0.04% | <0.04% |
| | (iii) Impurity-E | Degradant | <0.04% | <0.04% |
| | (iv) Ketopemetrexed | Degradant | <0.2% | <0.2% |
| | (v) Total degradation impurities | — | <0.6% | <0.6% |
| | (vi) Single specified impurity | — | <0.1% | <0.1% |
| | (viii) Single unspecified impurity | — | <0.2% | <0.2% |
| | (vi) Total impurities | — | <1% | <1% |

TABLE 10-continued

Physiological compatible study of Pemetrexed for Injection 100 mg/vial at a final concentration of 1 mg/mL with 0.9% sodium chloride solution for injection, USP

| S. No | Parameter | Type of impurities | Initial (Room Temperature) | 24 hours (2° C.-8° C.) |
|---|---|---|---|---|
| | (vii) Impurity-G** | chiral impurity | <0.05% | <0.05% |

TABLE 11

Physiological compatible study of Pemetrexed for Injection 100 mg/vial at a final concentration of 1 mg/mL with diluent, 5% Dextrose solution for Injection, USP

| S. No | Parameter | Type of impurities | Initial (Room Temperature) | 24 hours (2° C.-8° C.) |
|---|---|---|---|---|
| 1 | Assay by HPLC * | — | 103.9 | 102.6 |
| 2 | Description (After reconstitution) | — | Clear colorless solution | Clear colorless solution |
| 3 | pH | — | 6.36 | 6.33 |
| 4 | Osmolality (mOsmol/kg) | | 311 | 309 |
| 5 | Particulate matter | | | |
| | Foreign matter | — | Free from foreign matter | Free from foreign matter |
| | | — | 10 μm: 300<br>25 μm: 6/ | 10 μm: 226<br>25 μm: 14 |
| 6 | Related substance by HPLC (% w/w) | | | |
| | (i) Impurity-B | Degradant | <0.04% | <0.04% |
| | (ii) Impurity-C | Degradant | <0.04% | <0.04% |
| | (iii) Impurity-E | Degradant | <0.04% | <0.04% |
| | (iv) Ketopemetrexed | Degradant | <0.2% | <0.2% |
| | (v) Total degradation impurities | — | <0.6% | <0.6% |
| | (vi) Single specified impurity | — | <0.1% | <0.1% |
| | (viii) Single unspecified impurity | — | <0.2% | <0.2% |
| | (vi) Total impurities | — | <1% | <1% |
| | (vii) Impurity-G** | chiral impurity | <0.05% | <0.05% |

Conclusion: From the above physiological solution compatibility study results, it can be concluded that the Pemetrexed for Injection 100 mg/vial at a final concentration of 1 mg/mL is compatible with 0.9% Sodium Chloride Injection USP and 5% dextrose injection USP till 24 hours, when stored at refrigerated condition (2-8° C.).

Example 8: Physiological Solution Compatibility of Pemetrexed for Injection 500 mg/Vial Physiological solution compatible study of Pemetrexed for Injection 100 mg/vial (Batch #PEMAE1015) prepared according to Example 1 was executed using 0.9% sodium chloride solution for injection, USP and 5% dextrose solution for injection at a final concentration of pemetrexed as 1 mg/mL. The in-use stability of the final solution product was evaluated in accordance with the storage recommendations after reconstitution, at 2° C. to 8° C. up to 24 hours. Tables 12 and 13 (below) describe the results of physiological compatibility of pemetrexed for injection 100 mg/vial.

TABLE 12

Physiological compatible study of Pemetrexed for Injection 100 mg/vial at a final concentration of 1 mg/mL with 0.9% sodium chloride solution for injection, USP.

| S. No | Parameter | Type of impurities | Initial (Room Temperature) | 24 hours (2° C.-8° C.) |
|---|---|---|---|---|
| 1 | Assay by HPLC * | — | 98.2 | 98.6 |
| 2 | Description (After reconstitution) | — | Clear colorless solution | Clear colorless solution |
| 3 | pH | — | 6.93 | 6.94 |
| 4 | Particulate matter | | | |
| | Foreign matter | — | Free from foreign matter | Free from foreign matter |
| | | — | 10 μm: 422<br>25 μm: 28 | 10 μm: 396<br>25 μm: 20 |
| 5 | Related substance by HPLC (% w/w) | | | |
| | (i) Impurity-B | Degradant | 0.046 | 0.05 |
| | (ii) Impurity-C | Degradant | <0.04% | <0.04% |
| | (iii) Impurity-E | Degradant | <0.04% | <0.04% |
| | (iv) Ketopemetrexed | Degradant | <0.2% | <0.2% |
| | (v) Total degradation impurities | — | <0.6% | <0.6% |
| | (vi) Single specified impurity | — | <0.1% | <0.1% |
| | (viii) Single unspecified impurity | — | <0.2% | <0.2% |
| | (vi) Total impurities | — | <1% | <1% |
| | (vii) Impurity-G** | chiral impurity | <0.05% | <0.05% |

TABLE 13

Physiological compatible study of Pemetrexed for Injection 100 mg/vial at a final concentration of 1 mg/mL with diluent 5% Dextrose Injection, USP

| S. No | Parameter | Type of impurities | Initial (Room Temperature) | 24 hours (2° C.-8° C.) |
|---|---|---|---|---|
| 1 | Assay by HPLC * | — | 97.5 | 95.8 |
| 2 | Description (After reconstitution) | — | Clear colorless solution | Clear colorless solution |
| 3 | pH | — | 6.83 | 6.85 |
| 4 | Osmolality (mOsmol/kg) | | 336 | 339 |
| 5 | Particulate matter | | | |
| | Foreign matter | — | Free from foreign matter | Free from foreign matter |
| | | — | 10 μm: 740<br>25 μm: 46 | 10 μm:168<br>25 μm: 6 |
| 6 | Related substance by HPLC (% w/w) | | | |
| | (i) Impurity-B | Degradant | <0.04% | 0.047 |
| | (ii) Impurity-C | Degradant | <0.04% | 0.046 |
| | (iii) Impurity-E | Degradant | <0.04% | <0.04% |
| | (iv) Ketopemetrexed | Degradant | <0.2% | <0.2% |
| | (v) Total degradation impurities | — | <0.6% | <0.6% |
| | (vi) Single specified impurity | — | <0.1% | <0.1% |
| | (viii) Single unspecified impurity | — | <0.2% | <0.2% |
| | (vi) Total impurities | — | <1% | <1% |
| | (vii) Impurity-G | chiral impurity | <0.05% | <0.05% |

Conclusion: From the above physiological solution compatibility study results, it can be concluded that the Pemetrexed for Injection 500 mg/vial at a final concentration of 5 mg/mL is compatible with 0.9% Sodium Chloride Injection, USP and 5% Dextrose Injection USP till 24 hours, when stored at refrigerated condition (2-8° C.).

What is claimed is:

1. A reconstitutable lyophilized pharmaceutical composition, comprising:

pemetrexed dipotassium in an amount of about 118.3 mg equivalent to 100 mg of pemetrexed; and mannitol in an amount of about 106 mg; or pemetrexed dipotassium in an amount of about 591.5 mg equivalent to 500 mg pemetrexed; and mannitol in an amount of about 500 mg; and a pH modifying component consisting essentially of hydrochloric acid; with the proviso that the pH modifying component does not include a hydroxide base;

wherein after storage for at least 12 months at 25° C., the composition comprises:

not more than 2% w/w total water content; and not more than 0.6% w/w total impurities, including total degradation impurities wherein the degradation impurities are selected from:

(a) Impurity-B in an amount that does not exceed 0.1% w/w;

(b) Impurity-C in an amount that does not exceed 0.1% w/w;

(c) Impurity-E in an amount that does not exceed 0.1% w/w;

(d) ketopemetrexed in an amount that does not exceed 0.2% w/w; and a combination of two or more thereof.

2. The composition according to claim 1, wherein the composition has a pH from 6.6 to 7.8, when measured after reconstitution with 0.9% sodium chloride for injection or 5% dextrose solution for injection.

3. The composition according to claim 1, wherein the composition has a pH from 6.8 to 7.1, when measured after reconstitution with 0.9% sodium chloride for injection or 5% dextrose solution for injection.

4. The composition according to claim 1, wherein the composition is provided in a sealed and sterile vial.

5. The composition according to claim 1, wherein the composition contains not more than 1% w/w total impurities; and not more than 0.6% w/w of total degradation impurities after storage for at least 24 months when stored at a temperature of 25° C.

6. The composition according to claim 1, wherein the composition contains not more than 1% w/w total impurities; and not more than 0.6% w/w of total degradation impurities after storage for at least 36 months when stored at a temperature of 25° C.

7. The composition according to claim 1, wherein the reconstitution time is less than about 70 seconds.

8. The composition according to claim 1, wherein the composition is prepared by a process comprising:

(a) dissolving the mannitol in water for injection at about 13±3° C.; to obtain a clear solution;

(b) adding a portion of the mannitol solution to a container containing pemetrexed dipotassium as pemetrexed dipotassium heptahydrate on an anhydrous basis to obtain a slurry;

(c) adding the slurry to the bulk of the mannitol solution and stirring until a clear solution is obtained;

(d) adjusting the pH of the clear solution with hydrochloric acid to from about 6.6 to about 7.8;

(e) adjusting the volume of the solution by adding water for injection to obtain a bulk solution with target drug concentration;

(f) sterilizing the bulk solution using a pre-sterilized 0.22 μm filter;

(g) aseptically transferring the sterile bulk solution to a vial and partially stoppering the vial under nitrogen wherein the bulk solution filled in the vial is cooled to about 8° C. for freeze drying;

wherein the freeze-drying process comprises:

(1) freezing the bulk solution in a vial in accordance with the following steps sequentially to perform annealing:

(A) exposing the bulk solution obtained from step (g) to a temperature ranging from about −30° C. to about −50° C. and holding it for from about 70 to about 90 minutes;

(B) exposing the product of step (A) to a temperature ranging from about −5° C. to about −15° C. and holding it for from about 50 to about 70 minutes;

(C) exposing the product of step (B) to a temperature ranging from about −30° C. to about −50° C. and holding it for from about 95 to about 125 minutes;

(2) performing a primary drying of the product of step (1) (C) at a temperature of from about −17° C. to about 25° C.; and (3) performing a secondary drying of the product of step (2) at about 45° C.;

(h) completely stoppering the vial after completion of the freeze-drying process under filtered nitrogen; and (i) sealing and packing the vial.

9. The composition according to claim 8, wherein the process further comprises an annealing process;

wherein when the composition comprises pemetrexed dipotassium in an amount of about 118.3 mg equivalent to 100 mg of pemetrexed, the annealing process comprises the following steps sequentially:

(a) freezing the composition solution at a temperature of about −36° C. and holding it for about 80 minutes;

(b) bringing the temperature to about −10° C. and holding it for about 60 minutes; and (c) freezing at a temperature of about −35° C. and holding it for about 100 minutes; and wherein when the composition comprises pemetrexed dipotassium in an amount of about 591.5 mg equivalent to 500 mg pemetrexed, the annealing process comprises the following steps sequentially:

(a) freezing the composition solution at a temperature of about −45° C. and holding it for about 80 minutes;

(b) bringing the temperature to about −10° C. and holding it for about 60 minutes; and (c) freezing at a temperature of about −45° C. and holding it for about 120 minutes.

10. The composition according to claim 9, wherein when the composition comprises pemetrexed dipotassium in an amount of about 118.3 mg equivalent to 100 mg of pemetrexed, the process further comprises a primary drying process comprising the following steps sequentially:

(a) freezing at a temperature of about −17° C. and holding it for about 800 minutes;

(b) bringing the temperature to about −5° C. and holding it for about 480 minutes; and (c) bringing the temperature to about 25° C. and holding it for 180 minutes; and wherein when the composition comprises pemetrexed dipotassium in an amount of about 591.5 mg equivalent to 500 mg pemetrexed, the process further comprises a primary drying process comprising the following steps sequentially:

(a) freezing at a temperature of about −17° C. and holding it for about 640 minutes;

(b) bringing the temperature to about −5° C. and holding it for about 1020 minutes;

(c) bringing the temperature to about 6° C. and holding it for about 60 minutes;

(d) bringing the temperature to about 15° C. and holding it for about 60 minutes; and (e) bringing the temperature to about 23° C. and holding it for about 60 minutes.

11. The composition according to claim 10, wherein when the composition comprises pemetrexed dipotassium in an amount of about 118.3 mg equivalent to 100 mg of pemetrexed, the process further comprises a secondary drying process comprising the step of treating the vial obtained after primary drying at about 45° C. and holding it for about 550 minutes; and wherein when the composition comprises pemetrexed dipotassium in an amount of about 591.5 mg equivalent to 500 mg pemetrexed, the process further comprises a secondary drying process comprising the step of treating the vial obtained after primary drying at about 45° C. and holding it for about 1150 minutes.

12. A method of treating non-squamous NSCLC or mesothelioma to a patient in need thereof, comprising administering:

(i) a reconstitutable lyophilized pharmaceutical composition comprising pemetrexed dipotassium in an amount of about 118.3 mg equivalent to 100 mg of pemetrexed; and mannitol in an amount of about 106 mg; or (ii) a reconstitutable lyophilized pharmaceutical composition comprising pemetrexed dipotassium in an amount of about 591.5 mg equivalent to 500 mg pemetrexed; and mannitol in an amount of about 500 mg; and a pH modifying component consisting essentially of hydrochloric acid; with the proviso that the pH modifying component does not include a hydroxide base;

wherein after at least 12 months at a temperature of 25° C., the composition comprises:

(a) not more than 1.2% w/w total impurities, of which total degradation impurities do not exceed 0.6% w/w; wherein the degradation impurities comprise impurity-E in an amount that does not exceed 0.1% w/w; and (b) not more than 2% w/w total water content.

13. The method according to claim 12, wherein the composition is reconstituted with 0.9% sodium chloride solution for injection or 5% dextrose solution for injection prior to being administered to a patient in need thereof; and wherein the composition has a pH of from about 6.8 to about 7.1 when measured after reconstitution.

14. The method according to claim 13, wherein the concentration of pemetrexed achieved after reconstitution is 25 mg/ml.

15. The method according to claim 13, wherein the reconstitution time of the composition is less than 70 seconds.

16. The method according to claim 13, wherein the reconstituted solution is free from particulate matter for at least 24 hours after reconstitution, when stored at 2-8° C.

* * * * *